United States Patent
Kozlov et al.

(10) Patent No.: US 11,345,958 B2
(45) Date of Patent: *May 31, 2022

(54) METHODS FOR PERFORMING MULTIPLEXED REAL-TIME PCR

(71) Applicant: Roche Molecular Systems, Inc., Pleasanton, CA (US)

(72) Inventors: Igor Kozlov, Danville, CA (US); Amar Gupta, Danville, CA (US); Randall Saiki, Alameda, CA (US); Alison Tsan, Danville, CA (US)

(73) Assignee: Roche Molecular Systems, Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/314,470

(22) Filed: May 7, 2021

(65) Prior Publication Data

US 2021/0269857 A1 Sep. 2, 2021

Related U.S. Application Data

(62) Division of application No. 15/705,821, filed on Sep. 15, 2017, now Pat. No. 11,034,997.

(60) Provisional application No. 62/536,871, filed on Jul. 25, 2017, provisional application No. 62/435,595, filed on Dec. 16, 2016, provisional application No. 62/395,325, filed on Sep. 15, 2016.

(51) Int. Cl.
| | | |
|---|---|---|
| C07H 21/04 | (2006.01) | |
| C12Q 1/686 | (2018.01) | |
| C12Q 1/6823 | (2018.01) | |
| C12Q 1/6811 | (2018.01) | |
| C12Q 1/6883 | (2018.01) | |
| C12Q 1/6804 | (2018.01) | |
| C12Q 1/6818 | (2018.01) | |
| C12Q 1/6837 | (2018.01) | |

(52) U.S. Cl.
CPC .......... *C12Q 1/686* (2013.01); *C12Q 1/6804* (2013.01); *C12Q 1/6811* (2013.01); *C12Q 1/6818* (2013.01); *C12Q 1/6823* (2013.01); *C12Q 1/6837* (2013.01); *C12Q 1/6883* (2013.01); *C12Q 2531/113* (2013.01); *C12Q 2537/143* (2013.01); *C12Q 2561/113* (2013.01); *C12Q 2600/16* (2013.01)

(58) Field of Classification Search
None
See application file for complete search history.

(56) References Cited

U.S. PATENT DOCUMENTS

| | | | | |
|---|---|---|---|---|
| 2014/0066330 A1* | 3/2014 | Becker | ................. | C12Q 1/6895 506/9 |
| 2014/0272955 A1* | 9/2014 | Gupta | ................... | C12Q 1/686 435/6.11 |

* cited by examiner

*Primary Examiner* — Suryaprabha Chunduru
(74) *Attorney, Agent, or Firm* — David J. Chang

(57) ABSTRACT

The present invention describes methods for performing higher multiplexed real-time PCR for detection and quantitation of target nucleic acids using tagged hydrolysis probes.

12 Claims, 12 Drawing Sheets
Specification includes a Sequence Listing.

METHODS FOR PERFORMING MULTIPLEXED REAL-TIME PCR

CROSS REFERENCE TO RELATED APPLICATIONS

This application is a divisional application of U.S. patent application Ser. No. 15/705,821 filed Sep. 15, 2017, which claims the benefit of priority to U.S. Provisional Application No. 62/395,325, filed on Sep. 15, 2016, U.S. Provisional Application No. 62/435,595, filed on Dec. 16, 2016, and U.S. Provisional Application No. 62/536,871, filed on Jul. 25, 2017, each of which is hereby incorporated in its entirety by reference.

REFERENCE TO SEQUENCE LISTING

This application contains a Sequence Listing submitted as an electronic text file named "33677_US2.txt", having a size in bytes of 2 kb, and created on Aug. 14, 2017. The information contained in this electronic file is hereby incorporated by reference in its entirety pursuant to 37 CFR § 1.52(e)(5).

FIELD OF THE INVENTION

The present invention relates to methods for polymerase chain reaction (PCR) particularly to methods for performing multiplexed real-time PCR.

BACKGROUND OF THE INVENTION

The polymerase chain reaction (PCR) has become a ubiquitous tool of biomedical research, disease monitoring and diagnostics. Amplification of nucleic acid sequences by PCR is described in U.S. Pat. Nos. 4,683,195, 4,683,202, and 4,965,188. PCR is now well known in the art and has been described extensively in the scientific literature. See PCR Applications, ((1999) Innis et al., eds., Academic Press, San Diego), PCR Strategies, ((1995) Innis et al., eds., Academic Press, San Diego); PCR Protocols, ((1990) Innis et al., eds., Academic Press, San Diego), and PCR Technology, ((1989) Erlich, ed., Stockton Press, New York). A "real-time" PCR assay is able to simultaneously amplify and detect and quantify the starting amount of the target sequence. The basic TaqMan real-time PCR assay using the 5'-to-3' nuclease activity of the DNA polymerase is described in Holland et al., (1991) Proc. Natl. Acad. Sci. 88:7276-7280 and U.S. Pat. No. 5,210,015. The real-time PCR without the nuclease activity (a nuclease-free assay) has been described in a U.S. application Ser. No. 12/330,694 filed on Dec. 9, 2008. The use of fluorescent probes in real-time PCR is described in U.S. Pat. No. 5,538,848.

A typical real-time PCR protocol with fluorescent probes involves the use of a labeled probe, specific for each target sequence. The probe is preferably labeled with one or more fluorescent moieties, which absorb and emit light at specific wavelengths. Upon hybridizing to the target sequence or its amplicon, the probe exhibits a detectable change in fluorescent emission as a result of probe hybridization or hydrolysis.

The major challenge of the real-time assay however remains the ability to analyze numerous targets in a single tube. In virtually every field of medicine and diagnostics, the number of loci of interest increases rapidly. For example, multiple loci must be analyzed in forensic DNA profiling, pathogenic microorganism detection, multi-locus genetic disease screening and multi-gene expression studies, to name a few.

With the majority of current methods, the ability to multiplex an assay is limited by the detection instruments. Specifically, the use of multiple probes in the same reaction requires the use of distinct fluorescent labels. To simultaneously detect multiple probes, an instrument must be able to discriminate among the light signals emitted by each probe. The majority of current technologies on the market do not permit detection of more than four to seven separate wavelengths in the same reaction vessel. Therefore, using one uniquely-labeled probe per target, no more than four to seven separate targets can be detected in the same vessel. In practice, at least one target is usually a control nucleic acid. Accordingly, in practice, no more than three to six experimental targets can be detected in the same tube. The use of fluorescent dyes is also limited due to the spectral width where only about six or seven dyes can be fit within the visible spectrum without significant overlap interference. Thus the ability to multiplex an assay will not keep pace with the clinical needs, unless radical changes in the amplification and detection strategy are made.

An additional ability to multiplex a real-time amplification reaction is provided by a post-PCR melting assay. See U.S. patent application Ser. No. 11/474,071, filed on Jun. 23, 2006. In a melting assay, the amplified nucleic acid is identified by its unique melting profile. A melting assay involves determining the melting temperature (melting point) of a double-stranded target, or a duplex between the labeled probe and the target. As described in U.S. Pat. No. 5,871,908, to determine melting temperature using a fluorescently labeled probe, a duplex between the target nucleic acid and the probe is gradually heated (or cooled) in a controlled temperature program. The dissociation of the duplex changes the distance between interacting fluorophores or between a fluorophore and a quencher. The interacting fluorophores may be conjugated to separate probe molecules, as described in U.S. Pat. No. 6,174,670. Alternatively, one fluorophore may be conjugated to a probe, while the other fluorophore may be intercalated into a nucleic acid duplex, as described in U.S. Pat. No. 5,871,908. As yet another alternative, the fluorophores may be conjugated to a single probe oligonucleotide. Upon the melting of the duplex, the fluorescence is quenched as the fluorophore to the quencher are brought together in the now single-stranded probe.

The melting of the nucleic acid duplex is monitored by measuring the associated change in fluorescence. The change in fluorescence may be represented on a graph referred to as "melting profile." Because different probe-target duplexes may be designed to melt (or reanneal) at different temperatures, each probe will generate a unique melting profile. Properly designed probes would have melting temperatures that are clearly distinguishable from those of the other probes in the same assay. Many existing software tools enable one to design probes for a same-tube multiplex assay with these goals in mind. For example, Visual OMP™ software (DNA Software, Inc., Ann Arbor, Mich.) enables one to determine melting temperatures of nucleic acid duplexes under various reaction conditions.

The method of multiplex PCR using color detection and subsequent post-amplification melting assay is described in U.S. Pat. No. 6,472,156. The number of targets detectable by such a method is a product of the number of detectable wavelengths and the number of distinguishable melting profiles. Therefore adding a melting assay to color detection was a step forward in the ability to detect multiple targets.

The post-amplification melting assay is most commonly used for qualitative purposes, i.e. to identify target nucleic acids, see U.S. Pat. Nos. 6,174,670, 6,427,156 and 5,871,908. It is known to obtain a melting peak by differentiating the melting curve function. Ririe et al. ("Product differentiation by analysis of DNA melting curves during the polymerase chain reaction," (1997) *Anal. Biochem.* 245: 154-160) observed that differentiation helps resolve melting curves generated by mixtures of products. After differentiation, the melting peaks generated by each component of the mixture become easily distinguishable. It was also previously known that the post-amplification melting signal, i.e. melting peak, is higher in proportion to the amount of the nucleic acid in the sample. For example, U.S. Pat. No. 6,245,514 teaches a post-amplification melt assay using a duplex-intercalating dye, to generate a derivative melting peak, and then, using proprietary software, to integrate the peak. The integration provides information about the efficiency of amplification and relative amount of the amplified nucleic acid.

In practice, it would be desirable to move beyond a qualitative assay and be able to quantify multiple targets in the same sample. See e.g. Sparano et al. "Development of the 21-gene assay and its application in clinical practice and clinical trials," *J. Clin. Oncol.* (2008) 26(5):721-728. The ability to quantify the amount of target is useful in clinical applications, such as determination of viral load in a patient's serum, measuring the level of expression of a gene in response to drug therapy or determining the molecular signature of a tumor to predict its response to therapy.

In a real-time PCR assay, the signal generated by the labeled probe can be used to estimate the amount of input target nucleic acid. The greater the input, the earlier the fluorescence signal crosses a predetermined threshold value (Ct). Therefore one can determine relative or absolute amounts of the target nucleic acid by comparing the samples to each other or to a control sample with known amount of nucleic acid. However, the existing methods are limited in their ability to simultaneously quantify multiple targets. As with the qualitative detection of multiple targets, the limiting factor is the availability of spectrally-resolvable fluorophores. As explained above, state-of-the-art fluorescent label technology is not able to obtain distinct signals from more than six or seven separate fluorescently labeled probes in the same tube. Therefore a radically different experimental approach is needed to permit amplification and detection of numerous nucleic acid targets during real-time PCR.

Many methods for detection of target nucleic acids are known. Currently available homogeneous assays for nucleic acid detection include the TaqMan®, Amplifluor®, dye-binding, allele-selective kinetic PCR and Scorpion® primer assays. These assay procedures are not readily multiplexed due to the requirement for a different dye for each target nucleic acid to be detected, and thus are limited in their potential for improvement. To overcome such limitations, several recent studies have disclosed the use of oligonucleotide probes containing a cleavable "tag" portion which can be readily separated and detected (e.g. see Chenna et al, U.S. Patent Application Publication No. 2005/0053939; Van Den Boom, U.S. Pat. No. 8,133,701). More recently, improved methods to perform multiplexed nucleic acid target identification by using structure based oligonucleotide probe cleavage have been described in U.S. Patent Application Publication No. 2014/0272955, U.S. 2015/0176075, and U.S. 2015/0376681, all incorporated by reference herein.

Further methods to detect target nucleic acid sequence from DNA or a mixture of nucleic acid by the use of a combination of "Probing and Tagging Oligonucleotide" (PTO) and "Capturing and Templating Oligonucleotide" (CTO) in a so-called PTO Cleavage and Extension assay have been described by Chun et al. in U.S. Pat. No. 8,809,239. However the need still exists for an accurate method to perform high throughput multiplex detection of target nucleic acids.

SUMMARY OF THE INVENTION

The present invention provides for novel methods for nucleic acid sequence detection, particularly detection of multiple target nucleic acids using a real-time PCR assay. The methods are performed by the use of novel oligonucleotide probes having two unique features, a non-complementary tag portion and a quenching molecule.

Therefore in one aspect, the invention provides for a method for amplification and detection of a target nucleic acid in a sample comprising the steps of: (a) contacting the sample containing the target nucleic acid in a single reaction vessel with (i) one pair of oligonucleotide primers, each oligonucleotide primer capable of hybridizing to opposite strands of a subsequence of the target nucleic acid; (ii) an oligonucleotide probe that comprises an annealing portion and a tag portion, wherein the tag portion comprises a nucleotide sequence non-complementary to the target nucleic acid sequence or a non-nucleotide molecule, wherein the annealing portion comprises a nucleotide sequence at least partially complementary to the target nucleic acid sequence and hybridizes to a region of the subsequence of the target nucleic acid that is bounded by the pair of oligonucleotide primers, wherein the probe further comprises an interactive dual label comprising a reporter moiety located on the tag portion or on the annealing portion and a first quencher moiety located on the annealing portion and wherein the reporter moiety is separated from the first quencher moiety by a nuclease susceptible cleavage site; and wherein the tag portion is reversibly bound in a temperature-dependent manner to a quenching molecule that comprises or is associated with one or more quencher moieties capable of quenching the reporter moiety when the quenching molecule is bound to the tag portion; (b) amplifying the target nucleic acid by PCR using a nucleic acid polymerase having 5' to 3' nuclease activity such that during an extension step of each PCR cycle, the nuclease activity of the polymerase allows cleavage and separation of the reporter moiety from the first quenching moiety on the annealing portion of the probe; (c) measuring a suppressed signal from the reporter moiety at a first temperature at which the quenching molecule is bound to the tag portion; (d) increasing temperature to a second temperature at which the quenching molecule is not bound to the tag portion; (e) measuring a temperature corrected signal from the reporter moiety at the second temperature; (f) obtaining a calculated signal value by subtracting the suppressed signal detected at the first temperature from the temperature corrected signal detected at the second temperature; (g) repeating steps (b) through (f) through multiple PCR cycles; (h) measuring the calculated signal values from the multiple PCR cycles to detect the presence of the target nucleic acid.

In one embodiment, the tag portion comprises a modification such that it is not capable of being extended by a nucleic acid polymerase. In one embodiment, the reporter moiety is on the tag portion of the oligonucleotide probe. In another embodiment, the reporter moiety is located on the annealing portion of the oligonucleotide probe and is able to interact in a temperature-dependent manner to the quenching molecule that comprises the second quencher moiety. In one embodiment, the tag portion comprises a nucleotide sequence non-complementary to the target nucleic acid sequence and the quenching molecule is an oligonucleotide comprising a nucleotide sequence at least partially complementary to the tag portion of the oligonucleotide probe and binds to the tag portion by hybridization. In another embodiment, the tag portion of the oligonucleotide probe or the quenching molecule or both the tag portion and the quenching molecule contain one or more nucleotide modifications. In yet another embodiment, the one or more nucleotide modifications is selected from the group consisting of Locked Nucleic Acid (LNA), Peptide Nucleic Acid (PNA), Bridged Nucleic Acid (BNA), 2'-O alkyl substitution, L-enantiomeric nucleotide, or combinations theoreof. In one embodiment, the reporter moiety is a fluorescent dye and the quencher moiety quenches a detectable signal from the fluorescent dye.

In another aspect, the invention provides for a method for detecting two or more target nucleic acid sequences in a sample comprising the steps of: (a) contacting the sample suspected of containing the two or more target nucleic acid sequences in a single reaction vessel with (i) a first pair of oligonucleotide primers with nucleotide sequences that are complementary to each strand of a first target nucleic acid sequence, and a second pair of oligonucleotide primers with nucleotide sequences that are complementary to each strand of a second target nucleic acid sequence; (ii) a first oligonucleotide probe comprising a nucleotide sequence at least partially complementary to the first target nucleic acid sequence and anneals within the first target nucleic acid sequence bounded by the first pair of oligonucleotide primers, wherein the first oligonucleotide probe comprises a fluorescent moiety capable of generating a detectable signal and a first quencher moiety capable of quenching the detectable signal generated by the fluorescent moiety, wherein the fluorescent moiety is separated the first quencher moiety by a nuclease susceptible cleavage site; (iii) a second oligonucleotide probe comprising two distinct portions, an annealing portion comprising a nucleotide sequence at least partially complementary to the second target nucleic acid sequence and anneals within the second target nucleic acid sequence bounded by the second pair of oligonucleotide primers, wherein the annealing portion comprises a second quencher moiety; and a tag portion attached to the 5' terminus or to the 3' terminus of the annealing portion or attached via a linker to a region of the annealing portion and comprising a nucleotide sequence that is non-complementary to the two or more target nucleic acid sequences, wherein the tag portion comprises a fluorescent moiety that is identical to the fluorescent moiety on the first oligonucleotide probe and whose detectable signal is capable of being quenched by the second quencher moiety on the annealing portion, wherein the fluorescent moiety is separated from the second quenching moiety by a nuclease susceptible cleavage site; (iv) a quenching oligonucleotide comprising a nucleotide sequence at least partially complementary to the tag portion of the second oligonucleotide probe and hybridizes to the tag portion to form a duplex, wherein the quenching oligonucleotide comprises a third quencher moiety which quenches the detectable signal generated by the fluorescent moiety on the tag portion when the quenching oligonucleotide is hybridized to the tag portion; (b) amplifying the first and second target nucleic acid sequences by polymerase chain reaction (PCR) using a nucleic acid polymerase having 5' to 3' nuclease activity such that during an extension step of each PCR cycle, the 5' to 3' nuclease activity of the nucleic acid polymerase allows cleavage and separation of the fluorescent moiety from the first quenching moiety on the first oligonucleotide probe, and cleavage and separation of the fluorescent moiety on the tag portion from the second quenching moiety on the annealing portion of the second oligonucleotide probe, wherein at the extension step the quenching oligonucleotide remains hybridized to the tag portion; (c) measuring a fluorescent signal at a first temperature at which the quenching oligonucleotide is hybridized to the tag portion from the second oligonucleotide probe; (d) increasing temperature to a second temperature, which is higher than the first temperature, at which the quenching oligonucleotide is not hybridized to the tag portion from the second oligonucleotide probe; (e) measuring a fluorescent signal at the second temperature; (f) obtaining a calculated signal value by subtracting the fluorescent signal detected at the first temperature from the fluorescent signal detected at the second temperature; (g) repeating steps (b) through (f) in multiple PCR cycles to produce desired quantity of amplification products from the first and second target nucleic acid sequences; (h) determining the presence of the first target nucleic acid sequence from the fluorescent signals detected at the first temperature from the multiple PCR cycles and the presence of the second target nucleic acid sequence from the calculated signal values from the multiple PCR cycles.

In one embodiment, the tag portion comprises a modification such that it is not capable of being extended by a nucleic acid polymerase. In another embodiment, the tag portion is attached to the 5' terminus of the annealing portion. In yet another embodiment, the tag portion is attached to the 3' terminus of the annealing portion. In yet another embodiment, the tag portion is attached via a linker to a region of the annealing portion. In another embodiment, the tag portion of the second oligonucleotide probe or the quenching oligonucleotide or both the tag portion and the quenching oligonucleotide contain one or more nucleotide modifications. In yet another embodiment, the one or more nucleotide modifications is selected from the group consisting of Locked Nucleic Acid (LNA), Peptide Nucleic Acid (PNA), Bridged Nucleic Acid (BNA), 2'-O alkyl substitution, L-enantiomeric nucleotide, or combinations theoreof.

In yet another aspect, the invention provides for a method for detecting two or more target nucleic acid sequences in a sample comprising the steps of: (a) contacting the sample suspected of containing the two or more target nucleic acid sequences in a single reaction vessel with (i) a first pair of oligonucleotide primers with sequences that are complementary to each strand of a first target nucleic acid sequence, and a second pair of oligonucleotide primers with sequences that are complementary to each strand of a second target nucleic acid sequence; (ii) a first oligonucleotide probe comprising two distinct portions, a first annealing portion comprising a sequence at least partially complementary to the first target nucleic acid sequence and anneals within the first target nucleic acid sequence bounded by the first pair of oligonucleotide primers, wherein the first annealing portion comprises a first quencher moiety; and a first tag portion attached to the 5' terminus or to the 3' terminus of the first annealing portion or attached via a linker to a region of the first annealing portion and comprising a nucleotide sequence that is non-complementary to the two or more target nucleic acid sequences, wherein the first tag portion comprises a fluorescent moiety whose detectable signal is capable of being quenched by the first quencher moiety on the first annealing portion, wherein the fluorescent moiety is separated from the first quenching moiety by a nuclease susceptible cleavage site; (iii) a first quenching oligonucleotide comprising a sequence at least partially complementary to the first tag portion of the first oligonucleotide probe and hybridizes to the first tag portion to form a duplex, wherein the first quenching oligonucleotide comprises a second quenching moiety which quenches the detectable signal generated by the fluorescent moiety on the first tag portion when the first quenching oligonucleotide is hybridized to the first tag portion; (iv) a second oligonucleotide probe comprising two distinct portions, a second annealing portion comprising a sequence at least partially complementary to the second target nucleic acid sequence and anneals within the second target nucleic acid sequence bounded by the second pair of oligonucleotide primers, wherein the second annealing portion comprises a third quencher moiety; and a second tag portion attached to the 5' terminus or to the 3' terminus of the second annealing portion or attached via a linker to a region of the second annealing portion and comprising a nucleotide sequence that is non-complementary to the two or more target nucleic acid sequences, and has a different nucleic sequence or different nucleotide modifications compared to the nucleotide sequence of the first tag portion of the first oligonucleotide probe, wherein the second tag portion comprises a fluorescent moiety that is identical to the fluorescent moiety on the first oligonucleotide probe and whose detectable signal is capable of being quenched by the third quencher moiety on the second annealing portion, wherein the fluorescent moiety is separated from the third quenching moiety by a nuclease susceptible cleavage site; (v) a second quenching oligonucleotide comprising a sequence at least partially complementary to the second tag portion of the second oligonucleotide probe and hybridizes to the second tag portion to form a duplex, wherein the second quenching oligonucleotide comprises a fourth quenching moiety which quenches the detectable signal generated by the fluorescent moiety on the second tag portion when the second quenching oligonucleotide is hybridized to the second tag portion; wherein the duplex between the second quenching oligonucleotide and the second tag portion of the second oligonucleotide probe has a higher melting temperature (Tm) value than the duplex between the first quenching oligonucleotide and the first tag portion of the first oligonucleotide probe; (b) amplifying the first and second target nucleic acid sequences by polymerase chain reaction (PCR) using a nucleic acid polymerase having 5' to 3' nuclease activity such that during an extension step of each PCR cycle, the 5' to 3' nuclease activity of the nucleic acid polymerase allows (i) cleavage and separation of the fluorescent moiety on the first tag portion from the first quenching moiety on the first annealing portion of the first oligonucleotide probe, wherein at the extension step the first quenching oligonucleotide remains hybridized to the first tag portion, and (ii) cleavage and separation of the fluorescent moiety on the second tag portion from the third quenching moiety on the second annealing portion of the second oligonucleotide probe, wherein at the extension step the second quenching oligonucleotide remains hybridized to the second tag portion; (c) increasing temperature to a first temperature at which the first quenching oligonucleotide is not hybridized to the first tag portion from the first oligonucleotide probe and the second quenching oligonucleotide remains hybridized to the second tag portion from the second oligonucleotide probe; (d) measuring a fluorescent signal at the first temperature; (e) increasing temperature to a second temperature at which the second quenching oligonucleotide is not hybridized to the second tag portion from the second oligonucleotide probe; (f) measuring a fluorescent signal at the second temperature; (g) obtaining a calculated signal value by subtracting the fluorescent signal detected at the first temperature from the fluorescent signal detected at the second temperature; (h) repeating steps (b) through (g) in multiple PCR cycles to produce desired quantity of amplification products from the first and second target nucleic acid sequences; (I) determining the presence of the first target nucleic acid sequence from the fluorescent signals detected at the first temperature from the multiple PCR cycles and the presence of the second target nucleic acid sequence from the calculated signal values from the multiple PCR cycles.

In one embodiment, the first tag portion and the second tag portion both comprise a modification such that both tag portions are not capable of being extended by a nucleic acid polymerase.

In one embodiment, the first tag portion is attached to the 3' terminus of the first annealing portion of the first oligonucleotide probe and the second tag portion is attached to the 3' terminus of the second annealing portion of the second oligonucleotide probe. In another embodiment, the first tag portion is attached to the 3' terminus of the first annealing portion of the first oligonucleotide probe and the second tag portion is attached to the 5' terminus of the second annealing portion of the second oligonucleotide probe. In another embodiment, the first tag portion is attached to the 3' terminus of the first annealing portion of the first oligonucleotide probe and the second tag portion is attached via a linker to a region of the second annealing portion of the second oligonucleotide probe.

In one embodiment, the first tag portion is attached to the 5' terminus of the first annealing portion of the first oligonucleotide probe and the second tag portion is attached to the 5' terminus of the second annealing portion of the second oligonucleotide probe. In another embodiment, the first tag portion is attached to the 5' terminus of the first annealing portion of the first oligonucleotide probe and the second tag portion is attached to the 3' terminus of the second annealing portion of the second oligonucleotide probe. In another embodiment, the first tag portion is attached to the 5' terminus of the first annealing portion of the first oligonucleotide probe and the second tag portion is attached via a linker to a region of the second annealing portion of the second oligonucleotide probe.

In one embodiment, the first tag portion is attached via a linker to a region of the first annealing portion of the first oligonucleotide probe and the second tag portion is attached to the 5' terminus of the second annealing portion of the second oligonucleotide probe. In another embodiment, the first tag portion is attached via a linker to a region of the first annealing portion of the first oligonucleotide probe and the second tag portion is attached to the 3' terminus of the second annealing portion of the second oligonucleotide probe. In another embodiment, the first tag portion is attached via a linker to a region of the first annealing portion of the first oligonucleotide probe and the second tag portion is attached via a linker to a region of the second annealing portion of the second oligonucleotide probe.

In one embodiment, any of the first tag portion of the first oligonucleotide probe or the first quenching oligonucleotide or the second tag portion of the second oligonucleotide probe or the second quenching oligonucleotide or any combinations thereof contains one or more nucleotide modifications. In one embodiment, the one or more nucleotide modifications is selected from the group consisting of Locked Nucleic Acid (LNA), Peptide Nucleic Acid (PNA), Bridged Nucleic Acid (BNA), 2'-O alkyl substitution, L-enantiomeric nucleotide, or combinations theoreof.

In yet another aspect, the invention provides for a kit for detecting two or more target nucleic acid sequences in a sample comprising: (a) two or more pairs of oligonucleotide primers with sequences that are complementary to each strand of the two or more target nucleic acid sequences; (b) at least one oligonucleotide probe comprising two distinct portions, an annealing portion comprising a sequence at least partially complementary to one of the more than one target nucleic acid sequences and anneals within said one of the more than one target nucleic acid sequences, wherein the annealing portion comprises a first quencher moiety; and a tag portion attached to the 5' terminus or to the 3' terminus of the first annealing portion or attached via a linker to a region of the annealing portion, and comprising a nucleotide sequence that is non-complementary to the more than one target nucleic acid sequences, wherein the tag portion comprises a fluorescent moiety whose detectable signal is capable of being quenched by the first quencher moiety on the annealing portion, wherein said fluorescent moiety is separated from the first quenching moiety by a nuclease susceptible cleavage site; (c) at least one quenching oligonucleotide comprising a nucleotide sequence at least partially complementary to the tag portion of the oligonucleotide probe and hybridizes to the tag portion to form a duplex, wherein the quenching oligonucleotide comprises a second quencher moiety which quenches the detectable signal generated by the fluorescent moiety on the tag portion when the quenching oligonucleotide is hybridized to the tag portion. In one embodiment, the tag portion of the oligonucleotide probe or the quenching oligonucleotide or both the tag portion of the oligonucleotide probe and the quenching oligonucleotide contains one more nucleotide modifications wherein the one or more nucleotide modifications is selected from the group consisting of Locked Nucleic Acid (LNA), Peptide Nucleic Acid (PNA), Bridged Nucleic Acid (BNA), 2'-O alkyl substitution, L-enantiomeric nucleotide, or combinations theoreof.

DETAILED DESCRIPTION OF THE INVENTION

Definitions

Figure 1:
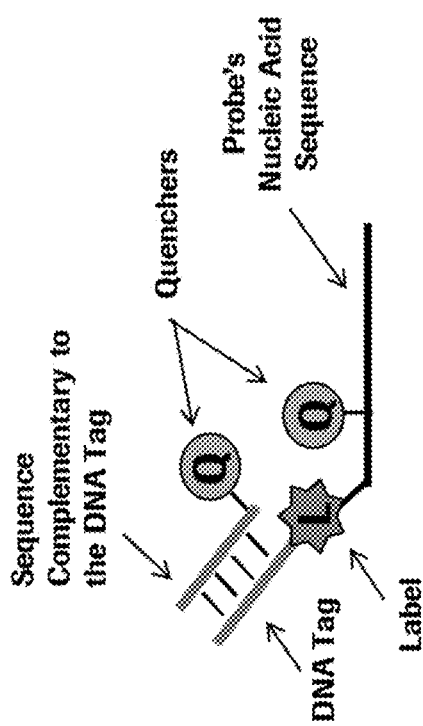
FIG. 1 is a graphical description of one embodiment of the oligonucleotide probe used to perform the methods of the invention.

The term "sample" as used herein includes a specimen or culture (e.g., microbiological cultures) that includes nucleic acids. The term "sample" is also meant to include both biological and environmental samples. A sample may include a specimen of synthetic origin. Biological samples include whole blood, serum, plasma, umbilical cord blood, chorionic villi, amniotic fluid, cerebrospinal fluid, spinal fluid, lavage fluid (e.g., bronchioalveolar, gastric, peritoneal, ductal, ear, arthroscopic), biopsy sample, urine, feces, sputum, saliva, nasal mucous, prostate fluid, semen, lymphatic fluid, bile, tears, sweat, breast milk, breast fluid, embryonic cells and fetal cells. In a preferred embodiment, the biological sample is blood, and more preferably plasma. As used herein, the term "blood" encompasses whole blood or any fractions of blood, such as serum and plasma as conventionally defined. Blood plasma refers to the fraction of whole blood resulting from centrifugation of blood treated with anticoagulants. Blood serum refers to the watery portion of fluid remaining after a blood sample has coagulated. Environmental samples include environmental material such as surface matter, soil, water and industrial samples, as well as samples obtained from food and dairy processing instruments, apparatus, equipment, utensils, disposable and non-disposable items. These examples are not to be construed as limiting the sample types applicable to the present invention.

The terms "target" or "target nucleic acid" as used herein are intended to mean any molecule whose presence is to be detected or measured or whose function, interactions or properties are to be studied. Therefore, a target includes essentially any molecule for which a detectable probe (e.g., oligonucleotide probe) or assay exists, or can be produced by one skilled in the art. For example, a target may be a biomolecule, such as a nucleic acid molecule, a polypeptide, a lipid, or a carbohydrate, which is capable of binding with or otherwise coming in contact with a detectable probe (e.g., an antibody), wherein the detectable probe also comprises nucleic acids capable of being detected by methods of the invention. As used herein, "detectable probe" refers to any molecule or agent capable of hybridizing or annealing to a target biomolecule of interest and allows for the specific detection of the target biomolecule as described herein. In one aspect of the invention, the target is a nucleic acid, and the detectable probe is an oligonucleotide. The terms "nucleic acid" and "nucleic acid molecule" may be used interchangeably throughout the disclosure. The terms refer to oligonucleotides, oligos, polynucleotides, deoxyribonucleotide (DNA), genomic DNA, mitochondrial DNA (mtDNA), complementary DNA (cDNA), bacterial DNA, viral DNA, viral RNA, RNA, message RNA (mRNA), transfer RNA (tRNA), ribosomal RNA (rRNA), siRNA, catalytic RNA, clones, plasmids, M13, P1, cosmid, bacteria artificial chromosome (BAC), yeast artificial chromosome (YAC), amplified nucleic acid, amplicon, PCR product and other types of amplified nucleic acid, RNA/DNA hybrids and polyamide nucleic acids (PNAs), all of which can be in either single- or double-stranded form, and unless otherwise limited, would encompass known analogs of natural nucleotides that can function in a similar manner as naturally occurring nucleotides and combinations and/or mixtures thereof. Thus, the term "nucleotides" refers to both naturally-occurring and modified/nonnaturally-occurring nucleotides, including nucleoside tri, di, and monophosphates as well as monophosphate monomers present within polynucleic acid or oligonucleotide. A nucleotide may also be a ribo; 2'-deoxy; 2',3'-deoxy as well as a vast array of other nucleotide mimics that are well-known in the art. Mimics include chain-terminating nucleotides, such as 3'-O-methyl, halogenated base or sugar substitutions; alternative sugar structures including nonsugar, alkyl ring structures; alternative bases including inosine; deaza-modified; chi, and psi, linker-modified; mass label-modified; phosphodiester modifications or replacements including phosphorothioate, methylphosphonate, boranophosphate, amide, ester, ether; and a basic or complete internucleotide replacements, including cleavage linkages such a photocleavable nitrophenyl moieties.

The presence or absence of a target can be measured quantitatively or qualitatively. Targets can come in a variety of different forms including, for example, simple or complex mixtures, or in substantially purified forms. For example, a target can be part of a sample that contains other components or can be the sole or major component of the sample. Therefore, a target can be a component of a whole cell or tissue, a cell or tissue extract, a fractionated lysate thereof or a substantially purified molecule. Also a target can have either a known or unknown sequence or structure.

The term "amplification reaction" refers to any in vitro means for multiplying the copies of a target sequence of nucleic acid.

"Amplifying" refers to a step of submitting a solution to conditions sufficient to allow for amplification. Components of an amplification reaction may include, but are not limited to, e.g., primers, a polynucleotide template, polymerase, nucleotides, dNTPs and the like. The term "amplifying" typically refers to an "exponential" increase in target nucleic acid. However, "amplifying" as used herein can also refer to linear increases in the numbers of a select target sequence of nucleic acid, but is different than a one-time, single primer extension step.

"Polymerase chain reaction" or "PCR" refers to a method whereby a specific segment or subsequence of a target double-stranded DNA, is amplified in a geometric progression. PCR is well known to those of skill in the art; see, e.g., U.S. Pat. Nos. 4,683,195 and 4,683,202; and PCR Protocols: A Guide to Methods and Applications, Innis et al., eds, 1990.

"Oligonucleotide" as used herein refers to linear oligomers of natural or modified nucleosidic monomers linked by phosphodiester bonds or analogs thereof. Oligonucleotides include deoxyribonucleosides, ribonucleosides, anomeric forms thereof, peptide nucleic acids (PNAs), and the like, capable of specifically binding to a target nucleic acid. Usually monomers are linked by phosphodiester bonds or analogs thereof to form oligonucleotides ranging in size from a few monomeric units, e.g., 3-4, to several tens of monomeric units, e.g., 40-60. Whenever an oligonucleotide is represented by a sequence of letters, such as "ATGCCTG," it will be understood that the nucleotides are in 5'-3' order from left to right and that "A" denotes deoxyadenosine, "C" denotes deoxycytidine, "G" denotes deoxyguanosine, "T" denotes deoxythymidine, and "U" denotes the ribonucleoside, uridine, unless otherwise noted. Usually oligonucleotides comprise the four natural deoxynucleotides; however, they may also comprise ribonucleosides or non-natural nucleotide analogs. Where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill.

As used herein "oligonucleotide primer", or simply "primer", refers to a polynucleotide sequence that hybridizes to a sequence on a target nucleic acid template and facilitates the detection of an oligonucleotide probe. In amplification embodiments of the invention, an oligonucleotide primer serves as a point of initiation of nucleic acid synthesis. In non-amplification embodiments, an oligonucleotide primer may be used to create a structure that is capable of being cleaved by a cleavage agent. Primers can be of a variety of lengths and are often less than 50 nucleotides in length, for example 12-25 nucleotides, in length. The length and sequences of primers for use in PCR can be designed based on principles known to those of skill in the art.

The term "oligonucleotide probe" as used herein refers to a polynucleotide sequence capable of hybridizing or annealing to a target nucleic acid of interest and allows for the specific detection of the target nucleic acid.

A "reporter moiety" or "reporter molecule" is a molecule that confers a detectable signal. The detectable phenotype can be colorimetric, fluorescent or luminescent, for example. A "quencher moiety" or "quencher molecule" is a molecule that is able to quench the detectable signal from the reporter moiety.

A "mismatched nucleotide" or a "mismatch" refers to a nucleotide that is not complementary to the target sequence at that position or positions. An oligonucleotide probe may have at least one mismatch, but can also have 2, 3, 4, 5, 6 or 7 or more mismatched nucleotides.

The term "polymorphism" as used herein refers to an allelic variant. Polymorphisms can include single nucleotide polymorphisms (SNP's) as well as simple sequence length polymorphisms. A polymorphism can be due to one or more nucleotide substitutions at one allele in comparison to another allele or can be due to an insertion or deletion, duplication, inversion and other alterations known to the art.

The term "modification" as used herein refers to alterations of the oligonucleotide probe at the molecular level (e.g., base moiety, sugar moiety or phosphate backbone). Nucleoside modifications include, but are not limited to, the introduction of cleavage blockers or cleavage inducers, the introduction of minor groove binders, isotopic enrichment, isotopic depletion, the introduction of deuterium, and halogen modifications. Nucleoside modifications may also include moieties that increase the stringency of hybridization or increase the melting temperature of the oligonucleotide probe. For example, a nucleotide molecule may be modified with an extra bridge connecting the 2' and 4' carbons resulting in locked nucleic acid (LNA) nucleotide that is resistant to cleavage by a nuclease (as described in Imanishi et al., U.S. Pat. No. 6,268,490 and in Wengel et al., U.S. Pat. No. 6,794,499, both of which are incorporated herein by reference in their entireties). The compositions of the tag portion of the oligonucleotide probe and of the quenching oligonucleotide molecule are only restricted by their ability to form stable duplexes. These oligonucleotides can therefore comprise of DNA, L-DNA, RNA, L-RNA, LNA, L-LNA, PNA (peptide nucleic acid, as described in Nielsen et al., U.S. Pat. No. 5,539,082), BNA (bridged nucleic acid, for example, 2',4'-BNA(NC) [2'-O,4'-C-aminomethylene bridged nucleic acid] as described in Rahman et al., J. Am. Chem. Soc. 2008; 130(14):4886-96), L-BNA etc. (where the "L-XXX" refers to the L-enantiomer of the sugar unit of the nucleic acids) or any other known variations and modifications on the nucleotide bases, sugars, or phosphodiester backbones.

Other examples of nucleoside modifications include various 2' substitutions such as halo, alkoxy and allyloxy groups that are introduced in the sugar moiety of oligonucleotides. Evidence has been presented that 2'-substituted-2'-deoxyadenosine polynucleotides resemble double-stranded RNA rather than DNA. Ikehara et al., (Nucleic Acids Res., 1978, 5, 3315) have shown that a 2'-fluro substituent in poly A, poly I, or poly C duplexed to its complement is significantly more stable than the ribonucleotide or deoxyribonucleotide poly duplex as determined by standard melting assays. Inoue et al., (Nucleic Acids Res., 1987, 15, 6131) have described the synthesis of mixed oligonucleotide sequences containing 2'-OMe (O-Methyl) substituents on every nucleic nucleotide. The mixed 2'-OMe-substituted oligonucleotide hybridized to its RNA complement as strongly as the RNA-RNA duplex which is significantly stronger than the same sequence RNA-DNA heteroduplex. Therefore, examples of substitutions at the 2' position of the sugar include F, CN, $CF_3$, $OCF_3$, OMe, OCN, O-alkyl, S-alkyl, SMe, $SO_2Me$, $ONO_2$, $NO_2$, $NH_3$, $NH_2$, NH-alkyl, $OCH_3=CH_2$ and OCCH.

The term "specific" or "specificity" in reference to the binding of one molecule to another molecule, such as a probe for a target polynucleotide, refers to the recognition, contact, and formation of a stable complex between the two molecules, together with substantially less recognition, contact, or complex formation of that molecule with other molecules. As used herein, the term "anneal" refers to the formation of a stable complex between two molecules.

A probe is "capable of annealing" to a nucleic acid sequence if at least one region of the probe shares substantial sequence identity with at least one region of the complement of the nucleic acid sequence. "Substantial sequence identity" is a sequence identity of at least about 80%, preferably at least about 85%, more preferably at least about 90%, 95% or 99%, and most preferably 100%. For the purpose of determining sequence identity of a DNA sequence and a RNA sequence, U and T often are considered the same nucleotide. For example, a probe comprising the sequence ATCAGC is capable of hybridizing to a target RNA sequence comprising the sequence GCUGAU.

The term "cleavage agent" as used herein refers to any means that is capable of cleaving an oligonucleotide probe to yield fragments, including but not limited to enzymes. For methods wherein amplification does not occur, the cleavage agent may serve solely to cleave, degrade or otherwise separate the second portion of the oligonucleotide probe or fragments thereof. The cleavage agent may be an enzyme. The cleavage agent may be natural, synthetic, unmodified or modified.

For methods wherein amplification occurs, the cleavage agent is preferably an enzyme that possesses synthetic (or polymerization) activity and nuclease activity. Such an enzyme is often a nucleic acid amplification enzyme. An example of a nucleic acid amplification enzyme is a nucleic acid polymerase enzyme such as *Thermus aquaticus* (Taq) DNA polymerase (TaqMan®) or *E. coli* DNA polymerase I. The enzyme may be naturally occurring, unmodified or modified.

A "nucleic acid polymerase" refers to an enzyme that catalyzes the incorporation of nucleotides into a nucleic acid. Exemplary nucleic acid polymerases include DNA polymerases, RNA polymerases, terminal transferases, reverse transcriptases, telomerases and the like.

A "thermostable DNA polymerase" refers to a DNA polymerase that is stable (i.e., resists breakdown or denaturation) and retains sufficient catalytic activity when subjected to elevated temperatures for selected periods of time. For example, a thermostable DNA polymerase retains sufficient activity to effect subsequent primer extension reactions, when subjected to elevated temperatures for the time necessary to denature double-stranded nucleic acids. Heating conditions necessary for nucleic acid denaturation are well known in the art and are exemplified in U.S. Pat. Nos. 4,683,202 and 4,683,195. As used herein, a thermostable polymerase is typically suitable for use in a temperature cycling reaction such as the polymerase chain reaction ("PCR"). The examples of thermostable nucleic acid polymerases include *Thermus aquaticus* Taq DNA polymerase, *Thermus* sp. Z05 polymerase, *Thermus flavus* polymerase, *Thermotoga maritima* polymerases, such as TMA-25 and TMA-30 polymerases, Tth DNA polymerase, and the like.

A "modified" polymerase refers to a polymerase in which at least one monomer differs from the reference sequence, such as a native or wild-type form of the polymerase or another modified form of the polymerase. Exemplary modifications include monomer insertions, deletions, and substitutions. Modified polymerases also include chimeric polymerases that have identifiable component sequences (e.g., structural or functional domains, etc.) derived from two or more parents. Also included within the definition of modified polymerases are those comprising chemical modifications of the reference sequence. The examples of modified polymerases include G46E E678G CS5 DNA polymerase, G46E L329A E678G CS5 DNA polymerase, G46E L329A D640G S671F CS5 DNA polymerase, G46E L329A D640G S671F E678G CS5 DNA polymerase, a G46E E678G CS6 DNA polymerase, Z05 DNA polymerase, ΔZ05 polymerase, ΔZ05-Gold polymerase, ΔZ05R polymerase, E615G Taq DNA polymerase, E678G TMA-25 polymerase, E678G TMA-30 polymerase, and the like.

The term "5' to 3' nuclease activity" or "5'-3' nuclease activity" refers to an activity of a nucleic acid polymerase, typically associated with the nucleic acid strand synthesis, whereby nucleotides are removed from the 5' end of nucleic acid strand, e.g., *E. coli* DNA polymerase I has this activity, whereas the Klenow fragment does not. Some enzymes that have 5' to 3' nuclease activity are 5' to 3' exonucleases. Examples of such 5' to 3' exonucleases include: Exonuclease from *B. subtilis*, Phosphodiesterase from spleen, Lambda exonuclease, Exonuclease II from yeast, Exonuclease V from yeast, and Exonuclease from *Neurospora crassa*.

The term "propanediol" or "propanediol spacer" refers to 1,3-Propanediol and is synonymous with Propane-1,3-diol, 1,3-Dihydroxypropane, and Trimethylene glycol. The term "HEG" or "HEG spacer" refers to hexaethylene glycol, which is synonymous with 3,6,9,12,15-Pentaoxaheptadecane-1,17-diol.

Various aspects of the present invention are based on a special property of nucleic acid polymerases. Nucleic acid polymerases can possess several activities, among them, a 5' to 3' nuclease activity whereby the nucleic acid polymerase can cleave mononucleotides or small oligonucleotides from an oligonucleotide annealed to its larger, complementary polynucleotide. In order for cleavage to occur efficiently, an upstream oligonucleotide must also be annealed to the same larger polynucleotide.

The detection of a target nucleic acid utilizing the 5' to 3' nuclease activity can be performed by a "TaqMan®" or "5'-nuclease assay", as described in U.S. Pat. Nos. 5,210, 015; 5,487,972; and 5,804,375; and Holland et al., 1988, Proc. Natl. Acad. Sci. USA 88:7276-7280, all incorporated by reference herein. In the TaqMan® assay, labeled detection probes that hybridize within the amplified region are present during the amplification reaction. The probes are modified so as to prevent the probes from acting as primers for DNA synthesis. The amplification is performed using a DNA polymerase having 5' to 3' exonuclease activity. During each synthesis step of the amplification, any probe which hybridizes to the target nucleic acid downstream from the primer being extended is degraded by the 5' to 3' exonuclease activity of the DNA polymerase. Thus, the synthesis of a new target strand also results in the degradation of a probe, and the accumulation of degradation product provides a measure of the synthesis of target sequences.

Any method suitable for detecting degradation product can be used in a 5' nuclease assay. Often, the detection probe is labeled with two fluorescent dyes, one of which is capable of quenching the fluorescence of the other dye. The dyes are attached to the probe, typically with the reporter or detector dye attached to the 5' terminus and the quenching dye attached to an internal site, such that quenching occurs when the probe is in an unhybridized state and such that cleavage of the probe by the 5' to 3' exonuclease activity of the DNA polymerase occurs in between the two dyes. Amplification results in cleavage of the probe between the dyes with a concomitant elimination of quenching and an increase in the fluorescence observable from the initially quenched dye. The accumulation of degradation product is monitored by measuring the increase in reaction fluorescence. U.S. Pat. Nos. 5,491,063 and 5,571,673, both incorporated by reference herein, describe alternative methods for detecting the degradation of probe which occurs concomitant with amplification.

A 5' nuclease assay for the detection of a target nucleic acid can employ any polymerase that has a 5' to 3' exonuclease activity. Thus, in some embodiments, the polymerases with 5'-nuclease activity are thermostable and thermoactive nucleic acid polymerases. Such thermostable polymerases include, but are not limited to, native and recombinant forms of polymerases from a variety of species of the eubacterial genera *Thermus, Thermatoga*, and *Thermosipho*, as well as chimeric forms thereof. For example, *Thermus* species polymerases that can be used in the methods of the invention include *Thermus aquaticus* (Taq) DNA polymerase, *Thermus thermophilus* (Tth) DNA polymerase, *Thermus* species Z05 (Z05) DNA polymerase, *Thermus* species sps17 (sps17), and *Thermus* species Z05 (e.g., described in U.S. Pat. Nos. 5,405,774; 5,352,600; 5,079,352; 4,889,818; 5,466,591; 5,618,711; 5,674,738, and 5,795,762. Thermatoga polymerases that can be used in the methods of the invention include, for example, *Thermatoga maritima* DNA polymerase and *Thermatoga neapolitana* DNA polymerase, while an example of a *Thermosipho* polymerase that can be used is *Thermosipho africanus* DNA polymerase. The sequences of *Thermatoga maritima* and *Thermosipho africanus* DNA polymerases are published in International Patent Application No. PCT/US91/07035 with Publication No. WO 92/06200. The sequence of *Thermatoga neapolitana* may be found in International Patent Publication No. WO 97/09451.

In the 5' nuclease assay, the amplification detection is typically concurrent with amplification (i.e., "real-time"). In some embodiments the amplification detection is quantitative, and the amplification detection is real-time. In some embodiments, the amplification detection is qualitative (e.g., end-point detection of the presence or absence of a target nucleic acid). In some embodiments, the amplification detection is subsequent to amplification. In some embodiments, the amplification detection is qualitative, and the amplification detection is subsequent to amplification.

In the present invention, real-time PCR amplification and detection of two or more target nucleic acid in a single reaction vessel (e.g. tube, well) may be performed using a standard TaqMan® oligonucleotide probe for detecting the presence of the first target and one or more novel TaqMan® oligonucleotide probes for detecting the presence of the second, third or more targets, with all the probes containing the same fluorescent label. Alternatively, the novel TaqMan® oligonucleotide probes may be used for detecting the presence of all the target nucleic acids. The novel probes have two distinguishing features.

The first feature of the novel probe is that it comprises two distinct portions. The first portion is referred as an annealing portion and comprises a sequence that is at least partially complementary to a target nucleic acid sequence such that it is capable of being hybridized with the target sequence. The annealing portion also contains a quencher moiety. In one embodiment, the annealing portion contains a reporter moiety such as a fluorescent dye that is capable of being quenched the quencher moiety and is separated from the quencher moiety by a nuclease susceptible cleavage site. The second portion of the oligonucleotide probe is referred as a tag portion. In one embodiment, the tag portion is attached to the 5' terminus of the annealing portion. In another embodiment, the tag portion is attached to the 3' terminus of the annealing portion. In another embodiment, the tag portion is attached anywhere between the 5' terminus and the 3' terminus of the annealing portion via a linker. The tag portion may comprise a nucleotide sequence that is not complementary to the target nucleic acid sequence and forms a "flap" region that is not capable of binding to the target nucleic acid (see FIG. 1 for a graphical representation of a 5' flap probe). The tag portion may also be comprised of non-nucleotides such as any organic moieties, or repeat units (e.g. $(CH_2—CH_2—O)_n$, etc.) as long as it can be attached to the annealing portion and can interact with a quenching molecule (as described in the following section). In one embodiment, the tag portion contains a reporter moiety such as a fluorescent dye that is capable of being quenched by the quencher moiety on the annealing portion. The annealing and tag portions of the oligonucleotide probe may optionally be separated by a non-nucleotide "linker". This linker can be comprised of carbon, carbon and oxygen, carbon and nitrogen, or any combination of these and can be of any length. Furthermore, the linker can be comprised of a linear moiety or a cyclic moiety. The linker may be derived from a single unit or from multiple identical or different units separated by phosphate linkages. The purpose of the linker is to create a region at the junction of the annealing and tag portions of the oligonucleotide probe. When the tag portion is separated from the annealing portion, the linker may also prevent the tag portion from being extended by a nucleic acid polymerase. Alternatively, another modification on the separated tag portion renders it non-extendible by the nucleic acid polymerase.

The second feature of the novel probe is that the tag portion binds to a quenching molecule. If the tag portion is a nucleotide sequence, the quenching molecule may be an oligonucleotide that is fully or partially complementary to the nucleotide sequence of the tag portion and hybridizes to the tag portion. The quenching molecule also contains or is associated with a quencher moiety, i.e. a second quencher moiety, which is also capable of quenching the signal from the reporter moiety (e.g. fluorescent dye) on the tag portion. The quencher moiety on or associated with the quenching molecule (the second quencher moiety) can be the same as or different from the quencher moiety on the annealing portion (the first quencher moiety). Therefore, prior to performing PCR amplification, the reporter moiety on the tag portion is quenched by both the quencher moiety on the annealing portion of the probe and by the quencher moiety on or associated with the quenching molecule (e.g. by a quenching oligonucleotide as shown in FIG. 1).

The general principle of using the novel probe to perform real-time PCR amplification and detection of target nucleic acid in a 5' nuclease assay is described below. First, a sample suspected of containing the target nucleic acid is provided. The sample is then contacted inside a single reaction vessel (e.g. a single test tube or a single well in a multi-well microplate) with PCR reagents that contain both the oligonucleotide primers capable of generating amplicons of the target nucleic acid and the novel oligonucleotide probe. PCR amplification begins by using a nucleic acid polymerase having 5' to 3' nuclease activity such that during the extension step of each PCR cycle, the nuclease activity of the polymerase allows cleavage and separation of the tag portion from the quenching moiety on the annealing portion of the probe. The separated tag portion may optionally contain a modification (such as the non-nucleotide linker) such that it is not capable of being extended by a nucleic acid polymerase.

Figure 2:
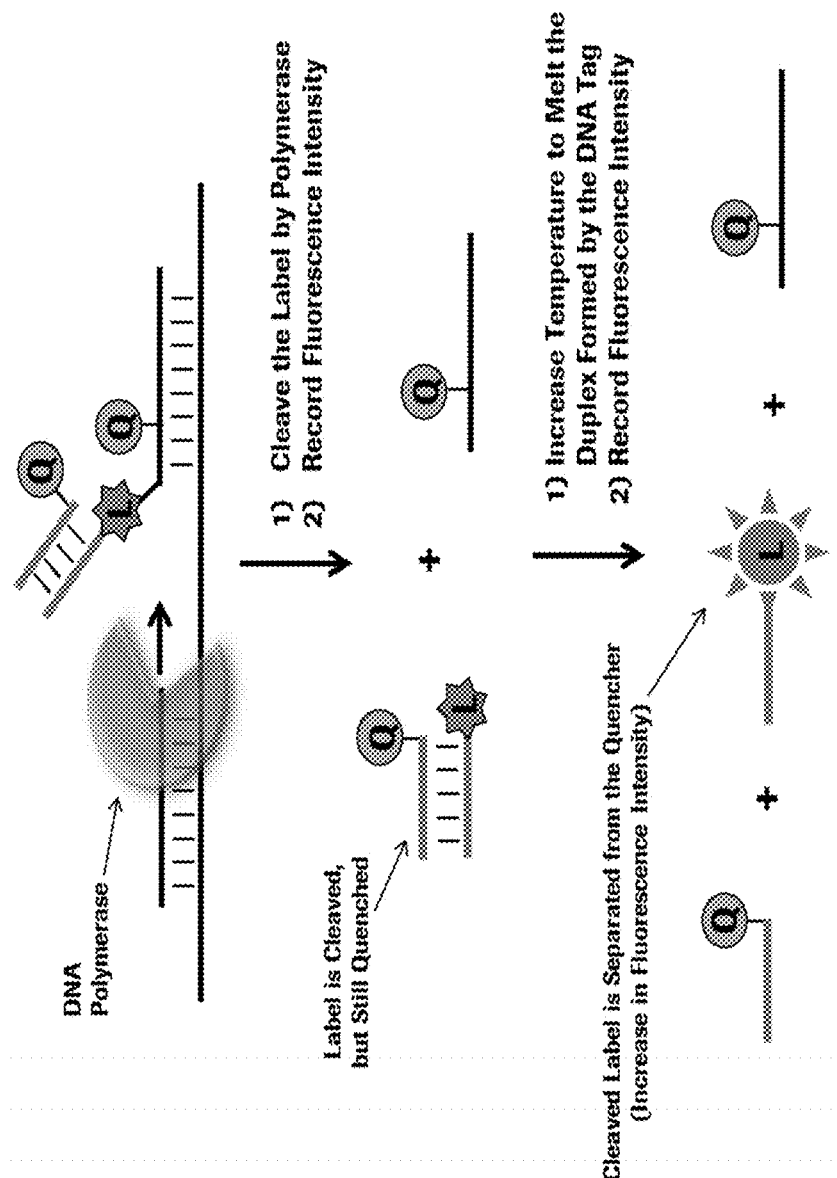
FIG. 2 is a graphical representation of the method of the invention that shows the separation of the tag portion and subsequent dissociation of the quenching oligonucleotide.
Figure 3:
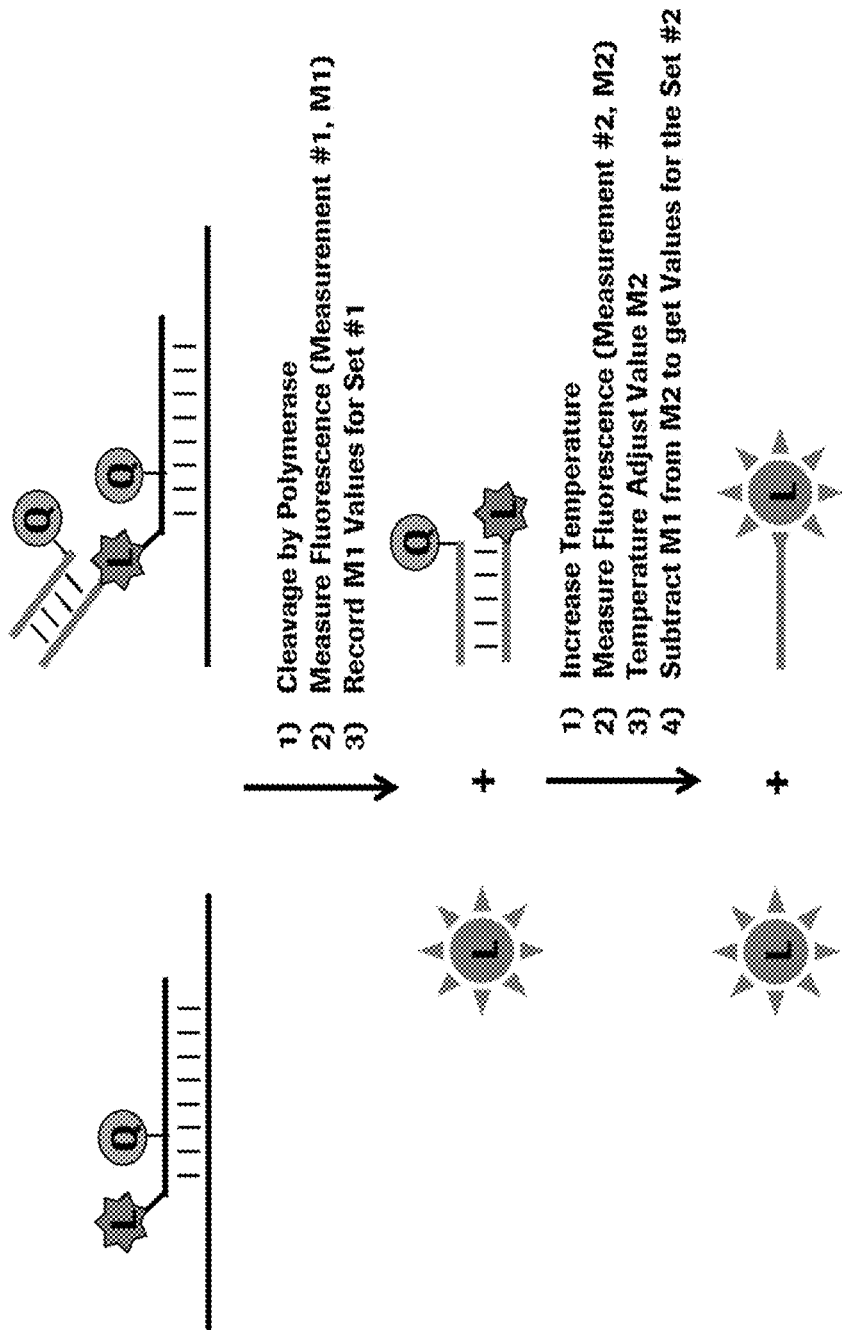
FIG. 3 is a description of one embodiment of the methods of the present invention.

Next, the signal from the reporter moiety on the separated tag portion is measured at a first temperature, usually, the annealing and/or extension temperature, at which the quenching molecule is still bound to the tag portion. Due to the presence of the quencher moiety on or associated with the quenching molecule, the signal from the reporter moiety (e.g. a fluorescent dye) on the tag portion is still quenched. Then, as a normal step in a PCR cycle, the temperature is gradually raised to the denaturation temperature. As the temperature increases from the extension temperature to the denaturation temperature, a temperature point is reached at which the quenching molecule is no longer bound to the tag portion. If the quenching molecule is an oligonucleotide that has sequences complementary to the nucleotide sequence of the tag portion, this dissociation occurs at the melting temperature (Tm) of the duplex formation between the quenching oligonucleotide molecule and the tag portion. Signal from the reporter moiety which is no longer quenched by the quencher moiety on or associated with the quenching oligonucleotide is then measured at a second temperature that is at or above the Tm temperature of the duplex. In fact, it may be better that the second temperature is above the Tm temperature to ensure that close to 100% of the tag portion are in single-stranded form. However, it is also possible to measure the signal at a temperature below the Tm temperature. Then, a calculated signal value is determined by subtracting the signal detected at the first temperature when the quenching molecule is still bound to the tag portion from the signal detected at the second temperature when the quenching molecule is not bound to the tag portion (see FIG. 2 and FIG. 3). The calculated signal value may optionally be normalized for correction of signals that may be affected by temperature. For example, fluorescent signals are known to decrease at higher temperatures, and therefore, standards can be used to normalize the signal values obtained at different temperatures.

These signal measurements and calculations are performed at multiple PCR cycles and the determined cumulative signal values can be used to determine not only the presence or absence but also the quantity of the target nucleic acid by determining the threshold value (Ct value) from a PCR growth curve generated from the signal values calculated plotted against PCR cycle number. In one embodiment, the signal measurements and calculations are performed at each PCR cycle.

Figure 4:
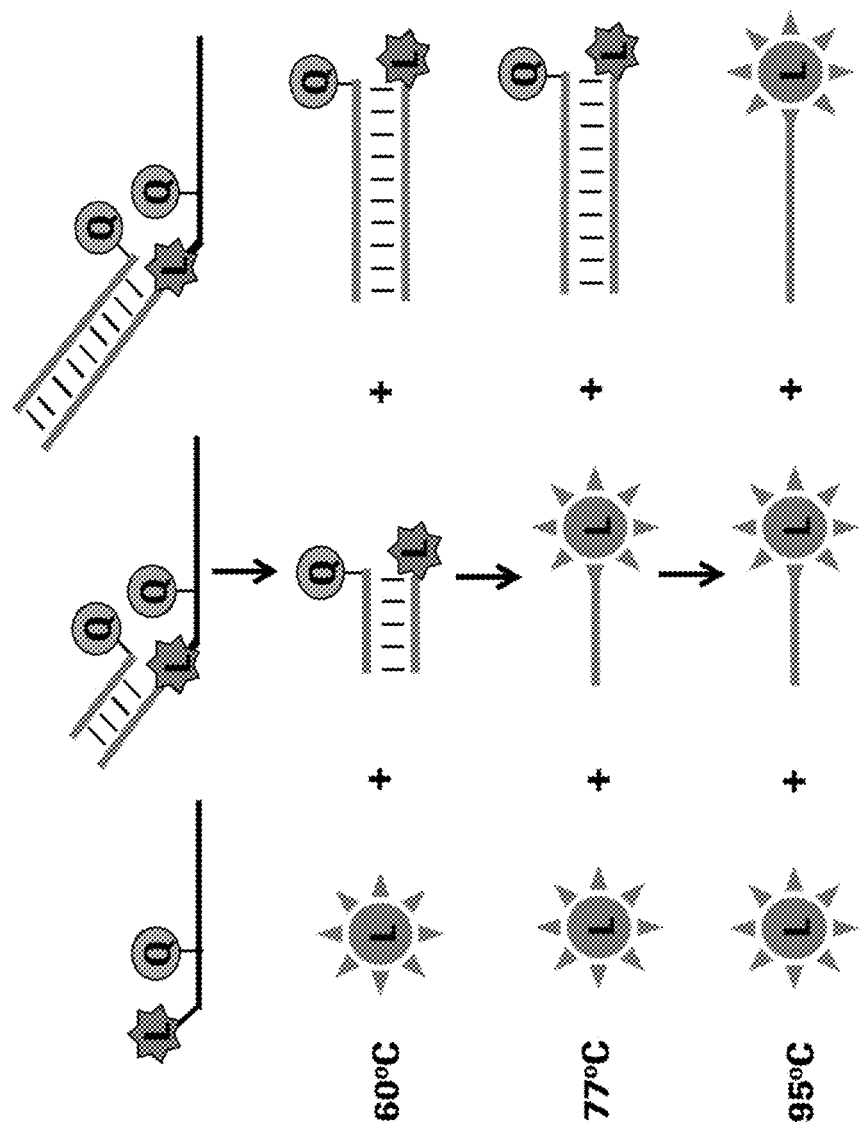
FIG. 4 shows the signal detection temperatures using another embodiment of the methods of the present invention.

Multiplex PCR assays using only one reporter moiety (e.g. one fluorescent dye) is possible by designing oligonucleotide probes that have tag portions hybridized to their respective quenching oligonucleotide molecules at various Tm temperatures. For example, amplification and detection of three target nucleic acid in one reaction can be achieved by using three oligonucleotide probes all labeled with the same fluorophore. A standard TaqMan® oligonucleotide probe may be used to detect the first target by measuring the fluorescent signal at a first temperature (usually the annealing temperature of a PCR cycle). A first "tagged" probe with a low Tm tag-quenching oligonucleotide duplex may be used to detect the second target by measuring the calculated fluorescent value at a second temperature at or above its Tm temperature and that is higher than the first temperature. A second "tagged" probe with a high Tm tag-quenching oligonucleotide duplex may be used to detect the third target by measuring the calculated fluorescent value at a third temperature at or above its Tm temperature and that is higher than the second temperature. (see FIG. 4) Theoretically, it would be possible to use one TaqMan® probe and two different tagged probes with four to seven different reporter moieties (e.g. fluorescent dyes) to detect between 12 and 21 different target nucleic acids in one reaction or one TaqMan® probe and 3 different tagged probes to detect between 16 and 28 different target nucleic acids in one reaction.

Additionally, the novel probes of the present invention can be designed such that the tag portion is a nucleotide sequence and is connected to a quenching oligonucleotide to form a hairpin (i.e. a stem-loop structure). In this structure, the "stem" portion will consist of the complementary regions between the tag portion and the quenching oligonucleotide while the "loop" portion may be comprised of non-complementary nucleotides or non-nucleotides such as linkers as previously described.

Figure 5:
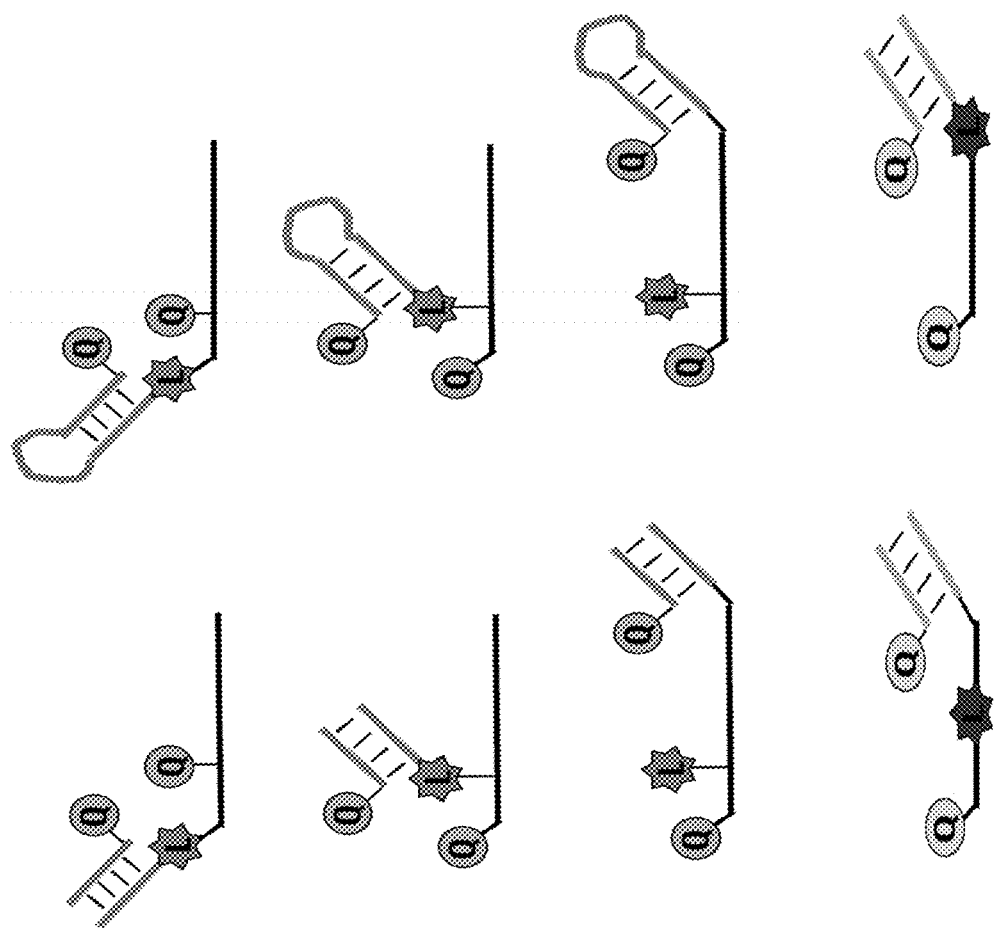
FIG. 5 shows different embodiments of the oligonucleotide probes used to practice the methods of the present invention.

Although the novel probes of the present invention have been described as having the reporter moiety located on the tag portion of the probes, it is also possible to position the reporter moiety on the annealing portion and place the first quencher moiety on the tag portion, as long as the reporter moiety can reversibly interact with the second quencher moiety on the quenching molecule. In a general sense, the reporter moiety is designed and positioned in the probe oligonucleotide in such a way that it is separated from the first quenching moiety on the annealing portion during the 5' nuclease (TaqMan®) assay and further designed to reversibly interact with the second quenching moiety on the quenching molecule. Some of these various alternate embodiments of the novel probes can be seen in FIG. 5.

In order to practice the methods of the present invention, certain features are necessary in the design of the tag portion of the probe oligonucleotide and of the quenching molecule. In one embodiment, both the tag portion and the quenching molecule are comprised of nucleotide sequences. In this situation, both the tag portion and the quenching oligonucleotide should not hybridize specifically to the target nucleic acid sequence but they should be fully or partially complementary to each other to allow hybridization at the desired temperatures. Both may include a modification at their 3' termini in order to not be extended by the nucleic acid polymerase during PCR amplification. Both the reporter moiety (e.g. fluorescent dye) on the tag portion and the quencher moiety on the quenching oligonucleotide can be located at the 5' terminus, the 3' terminus or at any position between the 5' and 3' termini but they must be located in proximity to each other when the tag portion is hybridized to the quenching oligonucleotide to allow the quenching moiety to quench the detectable signal from the reporter moiety.

With respect to different tag portions being hybridized to their respective quenching oligonucleotide molecules at various Tm temperatures, modified nucleotides can be introduced at all or some positions on either the tag portions, on the quenching oligonucleotides or on both the tag portions and the quenching oligonucleotides such that oligonucleotide length can be shortened. Examples of nucleotide modifications that serve to increase the melting temperature include LNA, PNA, G-clamp (9-(aminoethoxy)-phenoxazine-2'-deoxycytidine), propynyl deoxyuridine (pdU), propynyl deoxycytidine (pdC), and various 2' modifications at the sugar group, such as 2'-O-Methyl modifications. Another type of modification that may serve to prevent the unwanted binding of nucleic acid polymerase to the tag portion or to the quenching oligonucleotide would include the use of enantiomeric L-form of a nucleotide, such as L-DNA, L-RNA or L-LNA.

In another embodiment, the tag portion of the oligonucleotide probe and the quenching molecular are comprised of non-nucleotide molecules that reversibly interact with each other in a temperature-dependent manner. Examples of such non-nucleotide interactions include but are not limited to protein-protein interactions, protein-peptide interactions (e.g. peptide aptamers), protein-small molecule interactions, peptide-small molecule interactions, small molecule-small molecule interactions. In one example, the well-known interaction between biotin and avidin (or streptavidin) can be exploited by modifying either the biotin moiety (e.g. desthiobiotin) or the avidin moiety (see, Nordlund et al., *J. Biol. Chem.*, 2003, 278 (4) 2479-2483) or both in order to make the interaction reversible and temperature dependent.

In yet another embodiment, the interaction between the tag portion and the quenching molecule may involve interaction between a nucleotide sequence (or nucleotide sequences) and a non-nucleotide molecule in a sequence specific manner. Examples of these types of interactions include but are not limited to nucleic acid aptamers, DNA binding proteins or peptides and DNA minor groove binders. The design and synthesis of sequence-specific DNA-binding molecules have been described in several papers (see e.g. Dervan, *Science,* 1986, 232, 464-471; White et al., *Nature,* 1998, 391, 468-471) and these methods may be used to generate interactions between the tag portion and the quenching molecule that are temperature-dependent. Similarly, interactions between double stranded nucleotides and soluble quenchers can also be explored such that the quenching moiety does not need to be contained within the quenching molecule itself but may be in a soluble form that will interact with and quench the reporter moiety only when the tag portion is bound to the quenching molecule. Embodiments of the present invention will be further described in the following examples, which do not limit the scope of the invention described in the claims.

EXAMPLES

Example 1

Verification of Quenching by the Quenching Oligonucleotide

An experiment was performed to verify that a quenching oligonucleotide containing a quencher moiety would be able to hybridize with the fluorescently-labeled tag portion of an oligonucleotide probe and quench the fluorescent signal at a temperature below the melting temperature of the duplex but not at a temperature above the melting temperature in which the duplex has been dissociated. Table 1 contains the nucleotide sequences of the tag portion and the quenching oligonucleotide. Quenching oligonucleotide Q0 does not contain the quencher whereas quenching oligonucleotide Q1 contains a BHQ-2 quencher at its 5' terminus.

TABLE 1

| Name | Sequence | Modifications | SEQ ID NO: |
|---|---|---|---|
| 9FAM9TAG | CGTCGCCAGTCAGCTCCGG9F9T | 9 = C9 spacer, F = FAM | 1 |
| Q0 | CCGGAGCTGACTGGCGACGp | p = phosphate | 2 |
| Q1 | QCCGGAGCTGACTGGCGACGp | p = phosphate, Q = BHQ-2 | 3 |

The 9FAM9 TAG oligonucleotide was incubated without a quenching oligonucleotide (QX) or with the Q0 or Q1 quenching oligonucleotide at 1:5 molar ratio. The mixtures were then cycled in 50 µL reactions that consisted of 60 mM Tricine, 120 mM potassium acetate, 5.4% DMSO, 0.027% Sodium Azide, 3% glycerol, 0.02% Tween 20, 43.9 uM EDTA, 0.2 U/uL UNG, 0.1 uM 19TAGC9FAMC9, 0.5 uM Q0 or Q1, 400 µM dATP, 400 µM4CTP, 400 µM dGTP, 800

µM dUTP, and 3.3 mM Manganese Acetate. Cycle conditions resembling a typical PCR amplification reaction are shown on Table 2.

TABLE 2

| Step | Description | Cycle # | Temperature (° C.) | Time | Data acquisition |
|---|---|---|---|---|---|
| 1 | Sterilization/RT | 1 | 50 | 2 min | none |
|  |  |  | 94 | 5 sec | none |
|  |  |  | 55 | 2 min | none |
|  |  |  | 60 | 6 min | none |
|  |  |  | 65 | 4 min | none |
| 2 | Dark Cycles (no data acquisition) | 5 | 95 | 5 sec | none |
|  |  |  | 55 | 30 sec | none |
| 3 | TaqMan Cycles | 55 | 91 | 5 sec | none |
|  |  |  | 58 | 25 sec | fluorescence read |
|  |  |  | 80 | 5 sec | fluorescence read |

Figure 6:
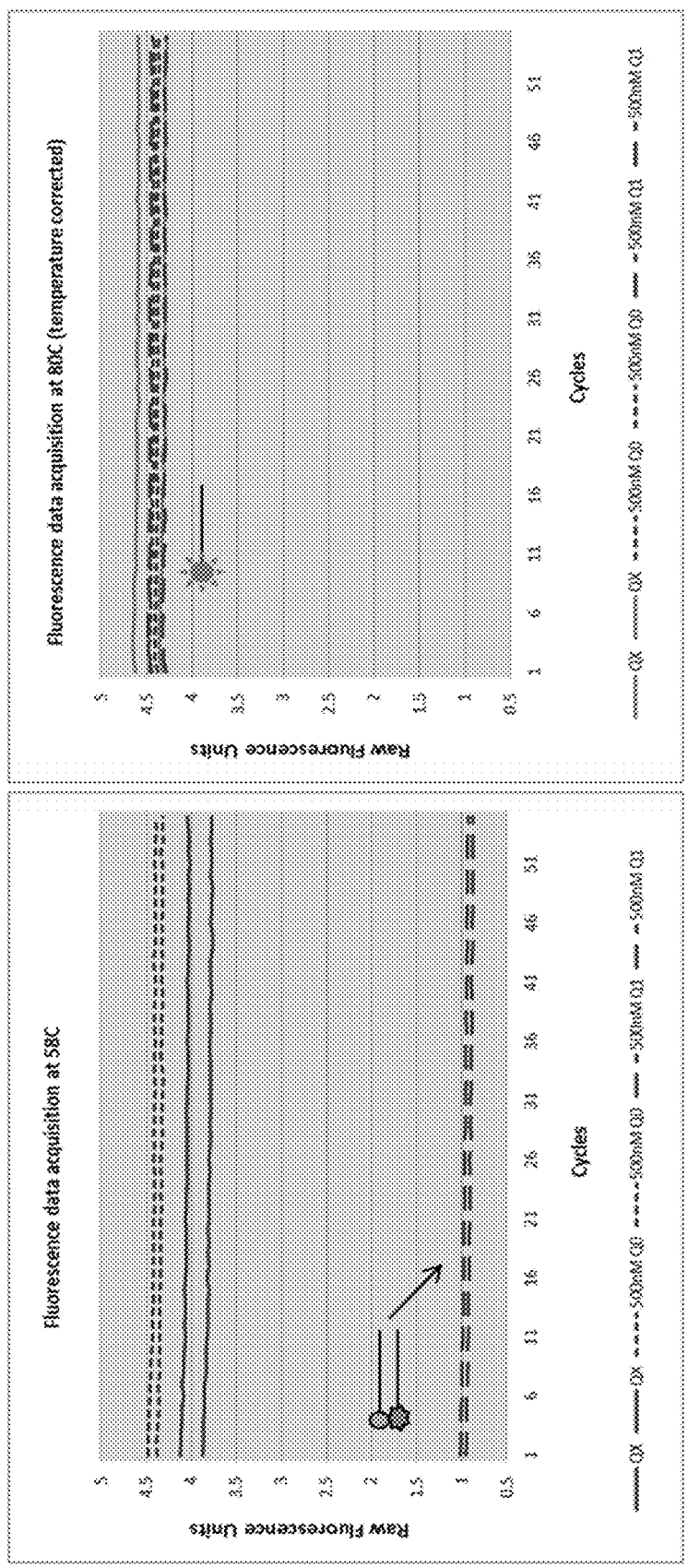
FIG. 6 shows the results of the hybridization and dissociation at two temperatures between a quenching oligonucleotide and a fluorescently labeled complementary oligonucleotide as described in Example 1.

The results of the experiment are shown on FIG. 6. When the signal from the FAM dye was measured at 58° C., fluorescence was detected with no quenching oligonucleotide (QX) or with a quenching oligonucleotide with no quenching moiety (Q0) but no signal was detected at any of the cycles in the presence of the Q1 quenching oligonucleotide. In contrast, when fluorescence was measured at 80° C., signals could be detected in all cycles even in the presence of the Q1 quenching oligonucleotide, which demonstrates that at the higher temperature, the Q1 quenching oligonucleotide was no longer hybridized with the TAG, and no quenching was observed.

Example 2

Real-Time PCR with Tagged Probe and Quenching Oligonucleotide

A Real-time PCR study was conducted using samples that contained various concentrations of an internal control template (GIC) mixed with various concentrations of a template sequence from HIV-1 Group M (HIM). A standard TaqMan® hydrolysis probe (G0) that hybridizes to the GIC sequence and a tagged probe (L24) with a complementary quenching oligonucleotide (Q9) and an annealing portion that hybridizes to the HIM sequence were used to detect the amplification products generated from these two templates. Both probes were labeled with FAM and Table 3 shows their sequences and the sequence of the quenching oligonucleotide.

TABLE 3

| Name | Sequence | Modifications | SEQ ID NO: |
|---|---|---|---|
| G0 | FTGCGCGTCCCGQTTTTGATACTT CGTAACGGTGCp | F = FAM, Q = BHQ-2, p = phosphate | 4 |
| L24 | QTCTCTAGCAGTGGCGCCCGAACA GGGACF CACACATTGGCACCGCCGTCTp | F = FAM, Q = BHQ-2, p = phosphate, tag underlined | 5 |
| Q9 | AGACGGCGGTGCCAATGTGTGQp | Q = BHQ-2, p = phosphate | 6 |

Four concentrations of GIC: 0 copies/reaction (cp/rxn), 100 cp/rxn, 1,000 cp/rxn, and 10,000 cp/rxn were mixed with four concentrations of HIM: 0 cp/rxn, 10 cp/rxn, 100 cp/rxn, and 1,000 cp/rxn to form sixteen different concentration combinations. PCR reagents and cycle conditions were as described in Example 1 and Table 2 with the exception that 100 nM of the G0 and L24 probes and 200 nM of the Q9 quenching oligonucleotide were used in the reactions. Fluorescence readings from the FAM label were taken at 58° C. and at 80° C. for each cycle beginning from cycle #6 (see Table 2).

Figure 7:
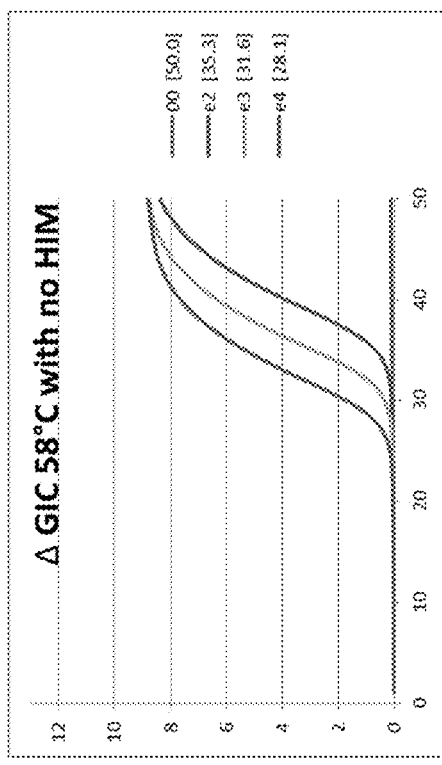
FIG. 7 shows the PCR growth curves generated from an internal control template (GIC) at 0, 100, 1,000 or 10,000 cp/rxn using a standard TaqMan® probe G0 and FAM fluorescence readings at 58° C. and in the absence of HIV-1 Group M template (HIM) (FIG. 7A) or in the presence of HIM at 10 cp/rxn (FIG. 7B), 100 cp/rxn (FIG. 7C) and 1,000 cp/rxn (FIG. 7D).
Figure 7:
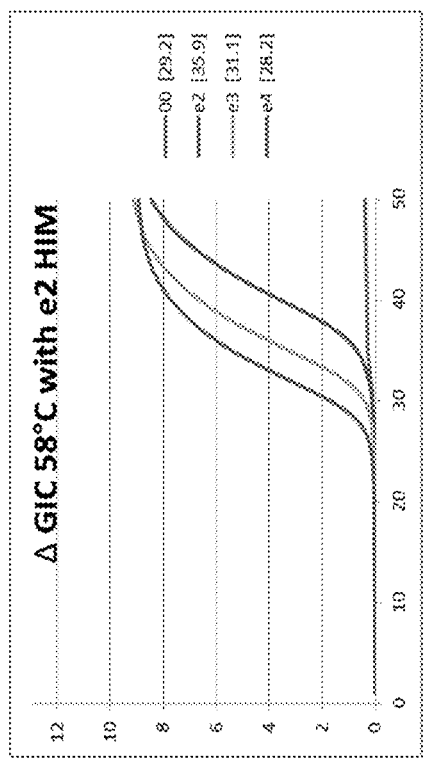
Figure 7:
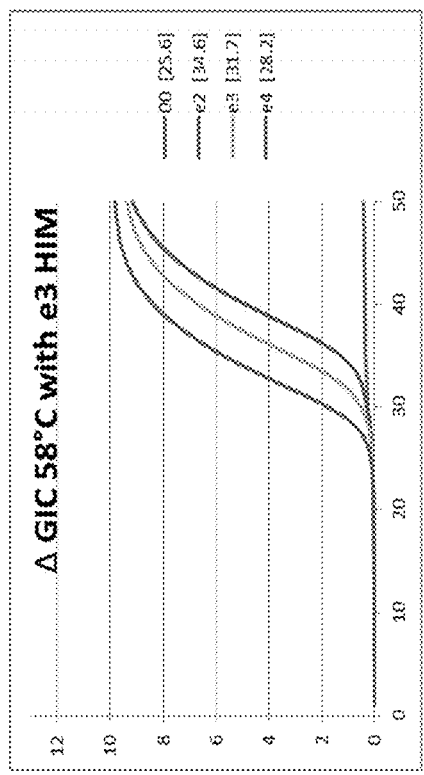
Figure 8:
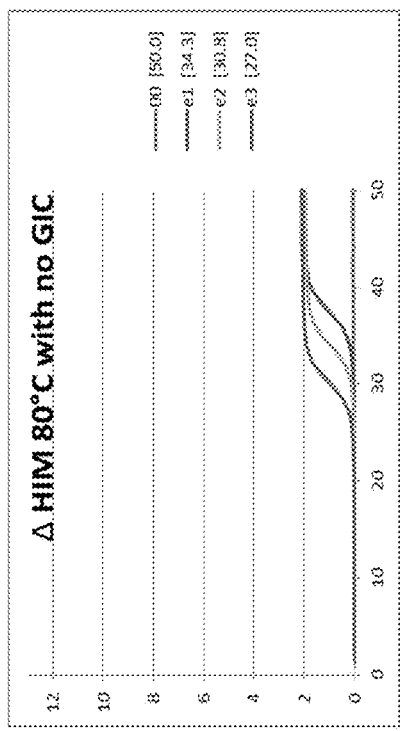
FIG. 8 shows the PCR growth curves generated from HIM at 0, 10, 100 or 1,000 cp/rxn using a tagged probe (L24) with a complementary quenching oligonucleotide (Q9) and FAM fluorescence readings at 80° C. and in the absence of GIC (FIG. 8A) or in the presence of GIC at 100 cp/rxn (FIG. 8B), 1,000 cp/rxn (FIG. 8C) and 10,000 cp/rxn (FIG. 8D).
Figure 8:
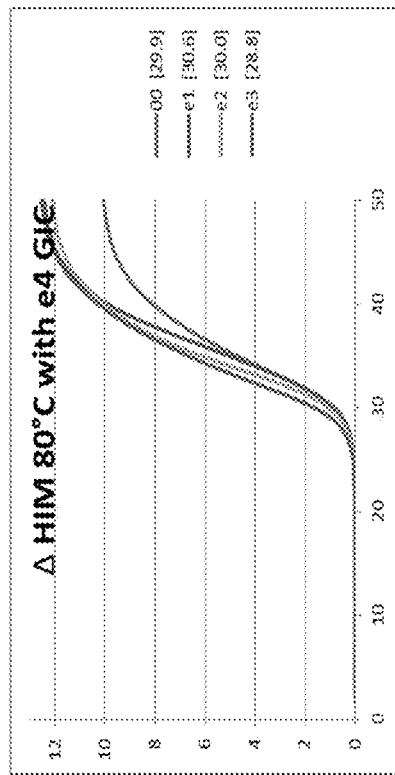
Figure 8:
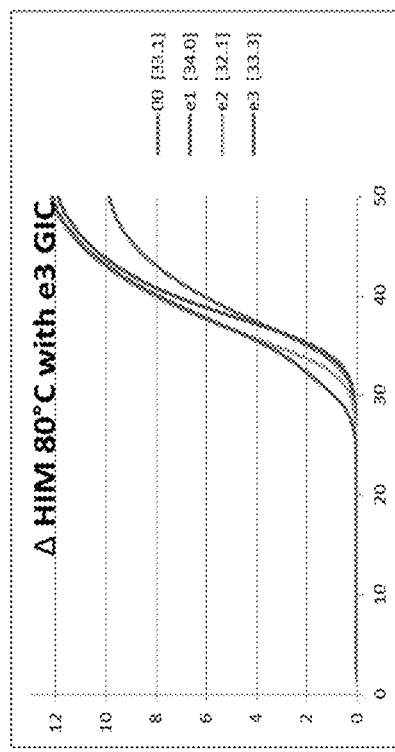
Figure 9:
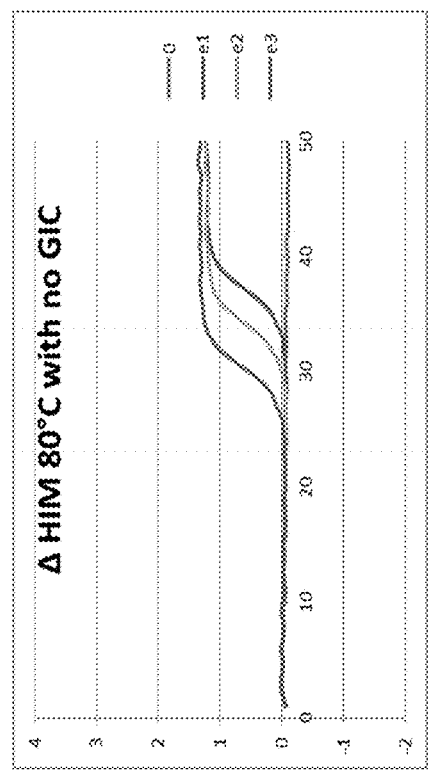
FIG. 9 shows the derived growth curves from HIM at 0, 10, 100 or 1,000 cp/rxn generated by having 84% of the 58° C. fluorescence signals subtracted from the 80° C. fluorescence signals in the absence of GIC (FIG. 9A) or in the presence of GIC at 100 cp/rxn (FIG. 9B), 1,000 cp/rxn (FIG. 9C) and 10,000 cp/rxn (FIG. 9D).
Figure 9:
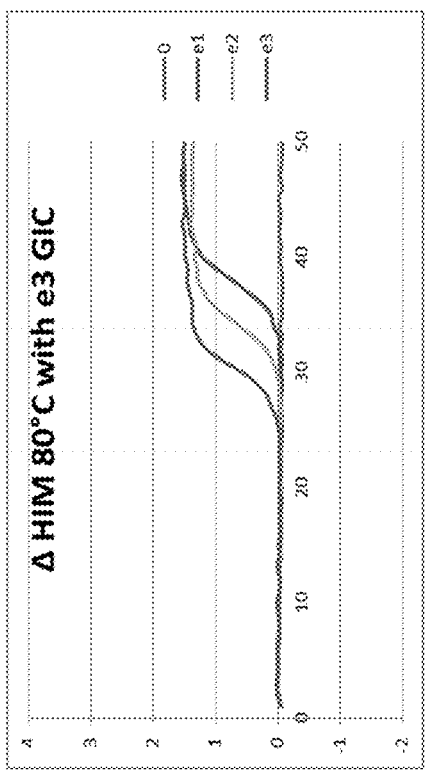

The results of these experiments are shown on FIGS. 7-9. The fluorescence readings at 58° C. are shown as growth curves in FIG. 7. FIG. 7A shows the growth curves generated with no HIM present and with 0, 100, 1,000 or 10,000 cp/rxn GIC. Interestingly, there are essentially no differences in the fluorescence intensities and the Cycle threshold (Ct) values in the growth curve readings at 58° C. in the presence of HIM at 10 cp/rxn (FIG. 7B), 100 cp/rxn (FIG. 7C) and 1,000 cp/rxn (FIG. 7D) which indicate that only the FAM signal from the standard TaqMan® G0 probe are detected at this temperature. This is because the FAM label on the L24 tagged probe is very efficiently quenched by the quencher on the Q9 quenching oligonucleotide and does not interfere with the detection of the GIC target.

The fluorescence readings at 80° C. are shown as growth curves in FIG. 8. FIG. 8A shows the growth curves generated with no GIC present and with 0, 10, 100 or 1,000 cp/rxn HIM. The fluorescence can now be detected from the FAM label on the L24 probe because it is no longer quenched by both the quencher on the "annealing portion" of the probe (due to hydrolysis by the nuclease) and the quencher on the quenching oligonucleotide (Q9) due to strand dissociation at this high temperature. Although the fluorescence intensity from the L24 probe is considerably lower than that of the G0 probe, it is still sufficient to calculate the Ct values that correspond to the starting concentrations of HIM. However, when HIM and GIC are both present, the fluorescence readings at 80° C. generate complex curves due to the stronger fluorescence that is detected from the G0 probe. (see FIG. 8B, 8C, 8D). Therefore, in order to "uncover" the fluorescent signal from the L24 tagged probe, it would be necessary to subtract out the fluorescent signal from the G0 probe, which would involve subtracting the 58° C. fluorescence readings (which is only contributed by the G0 probe) from the 80° C. fluorescence readings and derive growth curves that would resemble those observed in FIG. 8A.

When 100% of the 58° C. fluorescence readings were subtracted from the 80° C. fluorescence readings, the derived growth curves showed negative values which indicated that there was overcompensation of the subtraction. The reason for this observation was due to the reduced fluorescence intensity of the FAM label at 80° C. compared to the intensity at 58° C. Therefore, a "normalization" coefficient was deemed necessary and it was then empirically determined that 84% of the 58° C. signals subtracted from the 80° C. signals generated the best results. The derived growth curves are shown in FIGS. 9A, 9B, 9C and 9D and all are virtually identical to the 0 GIC growth curves of FIG. 8A. These results show that that fluorescent signals that indicate the presence of GIC can be separated from fluorescent signals that indicate the presence of HIM and demonstrate the multiplexing utility of the present invention.

Example 3

Real-Time PCR with Probes Having Different Fluorescent Dyes

Figure 10:
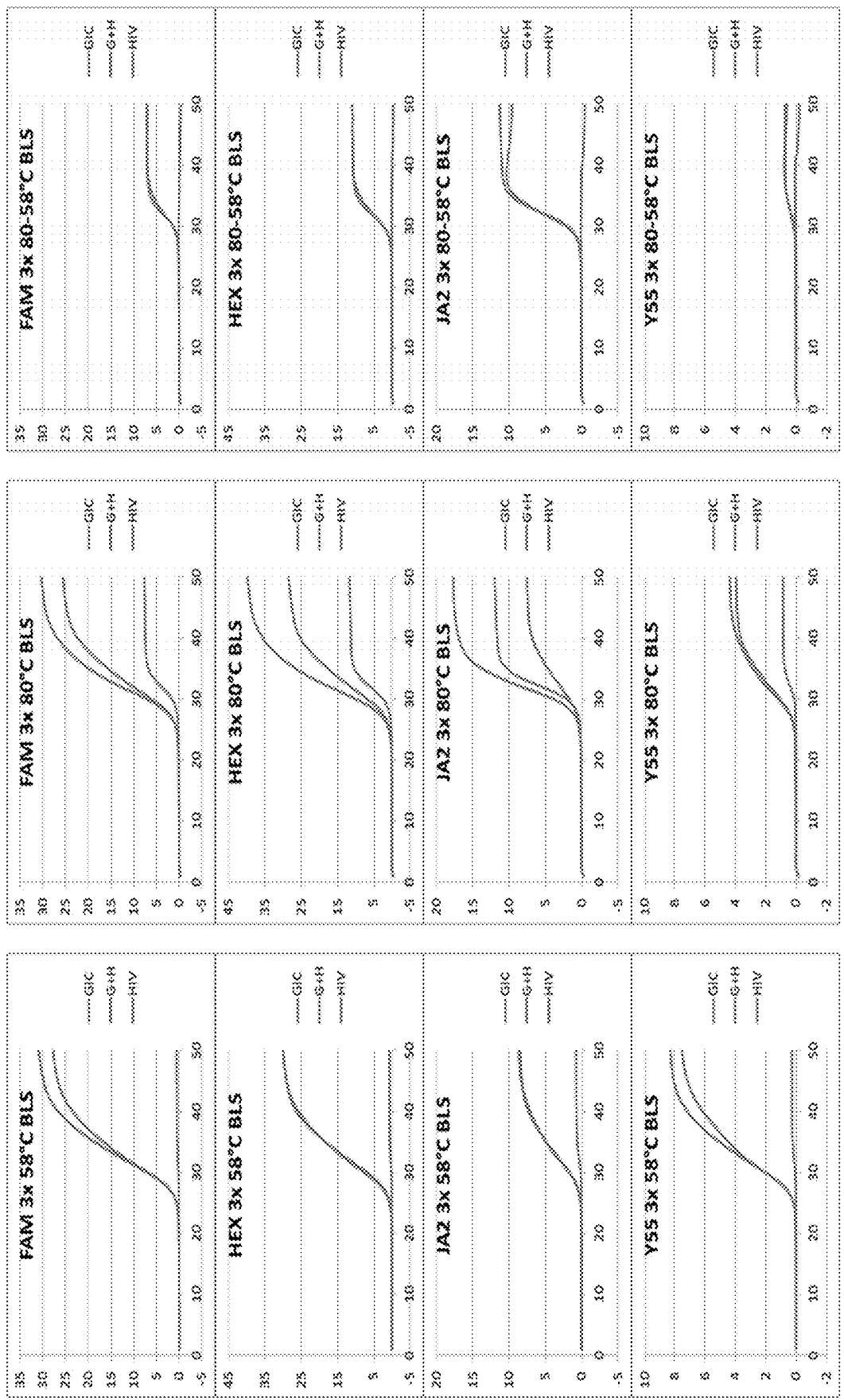
FIG. 10 shows the PCR growth curves generated from an internal control template (GIC) or an HIV template (HIV), or both GIC and HIV templates (G+H) using a standard TaqMan® GIC probe (G0) and a tagged HIV probe (L24) with complementary quenching oligonucleotide (Q9) in which both probes are labeled with FAM (1st row), with HEX ($2^{nd}$ with JA270 dye ($3^{rd}$ row) or with Cy5.5 ($4^{th}$ row).

A series of experiments were performed as described in Example 2 except that the G0 and L24 probes were labeled with FAM dye in the first set, with HEX dye in the second set, with JA270 dye in the third set and with Cy5.5 dye in the fourth set. In each set of experiments, PCR amplification was performed with only GIC template present at 100 cp/rxn, only HIV template present at 1000 cp/rxn or with both GIC (100 cp/rxn) and HIV (1000 cp/rxn) templates present. The results of the experiment are shown in FIG. 10. In fluorescence readings at 58° C. (FIG. 10, $1^{st}$ column), only signals generated by the G0 probes for the GIC templates were observed, as expected, since the L24 probes were still hybridized to the Q9 quenching oligonucleotides. In fluorescence readings at 80° C. (FIG. 10, $2^{nd}$ column), signals generated by both the G0 probes (for GIC) and the "unquenched" L24 probes for HIV) were observed. After using a normalized coefficient for each fluorescent dye, the 58° C. signals subtracted from the 80° C. signals generated the growth curves derived from the HIV template only (FIG. 10, $3^{rd}$ column). The signals generated from HEX and JA270 were similar or higher than the signals from FAM while the signals from Cy5.5 were considerably lower than FAM signals but nevertheless detectable.

Example 4

Real-Time PCR with L-DNA Tagged Probe and Quenching Oligonucleotide

Figure 11:
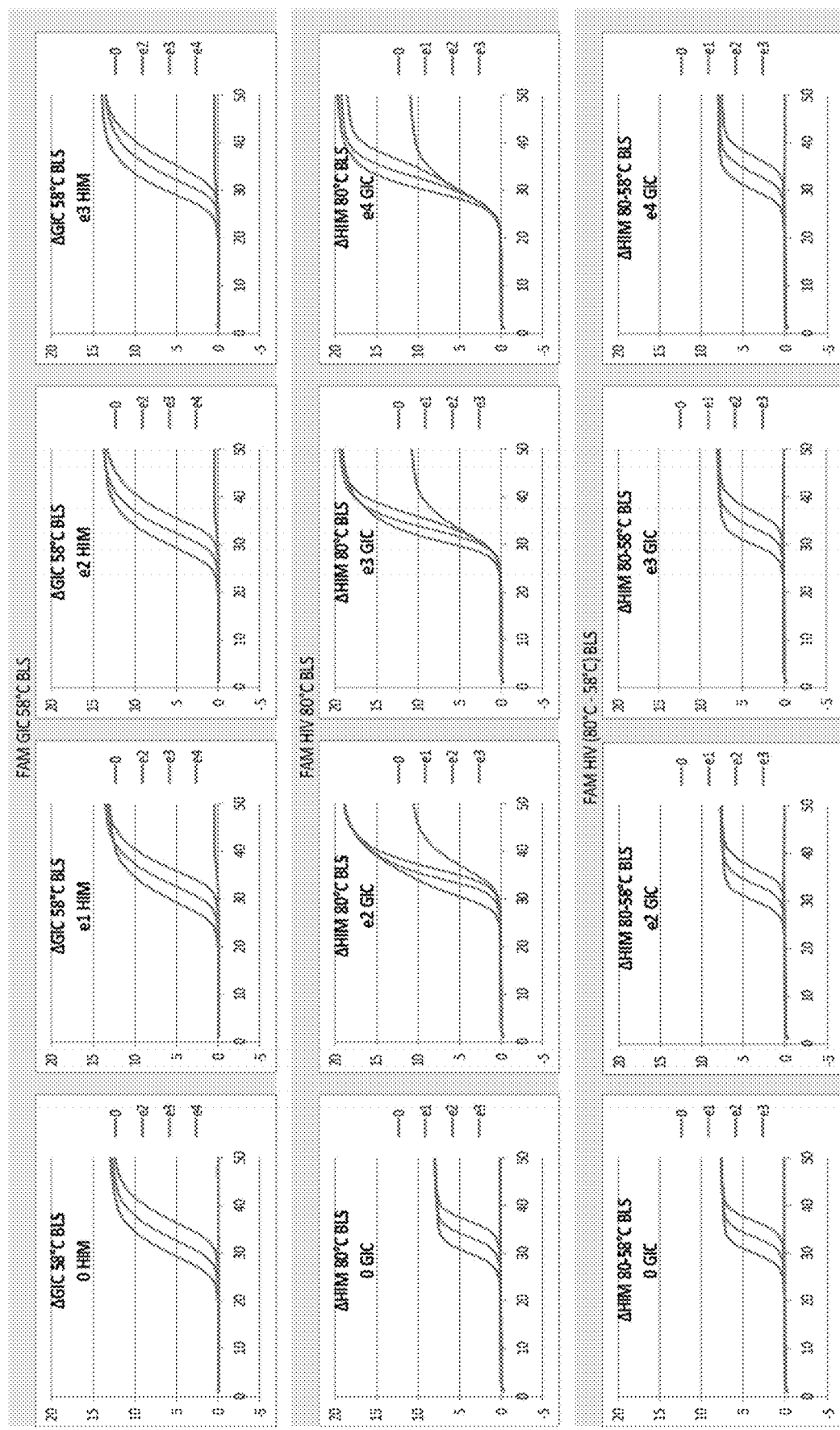
FIG. 11 shows the PCR growth curves of the experiment as described in Example 4 in which the L24 tagged probe contains L-DNA instead of D-DNA.

An experiment identical to the experiment described in Example 2 was performed with the exception that the L24 Tagged Probe to detect the HIV-1 Group M (HIM) template was comprised entirely of L-deoxyribose nucleotides instead of the "natural" D-deoxyribose nucleotides. The results of the experiment are shown in FIG. 11 where it was observed that the fluorescence signals generated by using the L-enantiomer form of the L24 tagged probe were 4-5 fold higher than the signals generated using the D-enantiomer form of the L24 tagged probe.

Example 5

Figure 12:
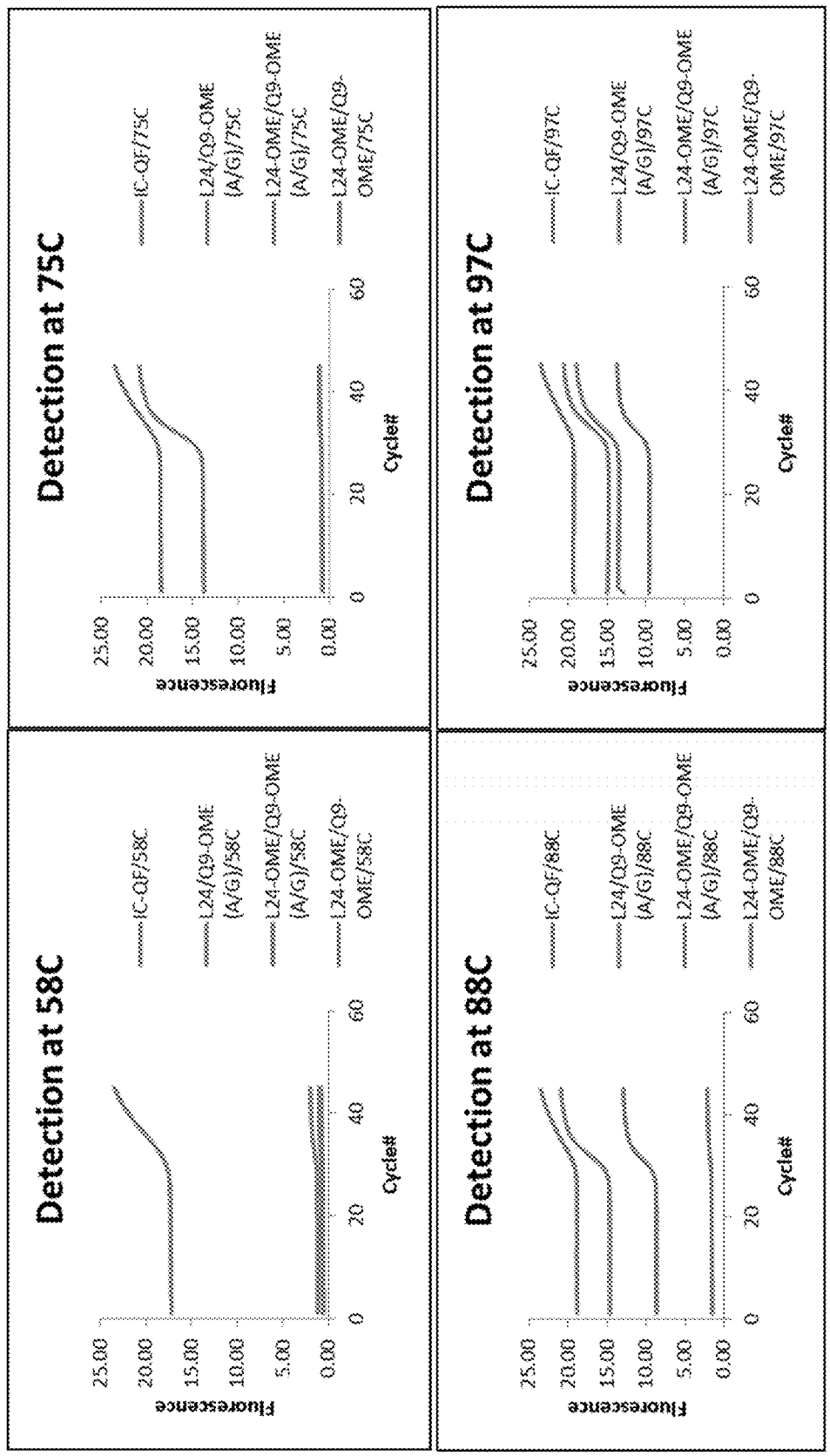
FIG. 12 shows the PCR growth curves of the experiment as described in Example 5 in which fluorescence signal detection was measured at 58° C., 75° C., 88° C. or 97° C. in the presence of a standard TaqMan® GIC probe (IC-QF), a tagged HIV probe (L24) with a quenching oligonucleotide that has A and G nucleotides modified with 2'-OMe substitutions (Q9-OMe A/G), a tagged HIV probe that has all nucleotides modified with 2'OMe substitutions (L24-OMe) with a quenching oligonucleotide (Q9-OMe A/G), and a tagged HIV probe (L24-OMe) with a quenching oligonucleotide that has all nucleotides modified with 2'-OMe substitutions (Q9-OMe).

Real-Time PCR with Tagged Probes and Quenching Oligonucleotides Having 2'-O Methyl Modifications An experiment similar to the one described in Example 2 was performed except that tagged probes and quenching oligonucleotides having nucleotide modifications were used. In addition to the "standard" L24 probe used to detect the presence of the HIM template, the tagged probe, L24-OME was generated in which every nucleotide in the tag portion of the probe (shown in TABLE 3 as the underlined portion of L24) was modified by having an O-Methyl substituent on the 2' position of the ribose moiety (2'-OMe). Two modified Q9 quenching oligonucleotides for hybridizing to the tag portion of L24 were also generated. Q9-OME had every nucleotide modified by a 2'-OMe substituent, and Q9-OME (A/G) had only the A and G nucleotides modified by a 2'-OMe substituent. Detection of the HIM template was performed using three different combinations of the tag portion and quenching oligonucleotide: L24 with Q9-OME (A/G), L24-OME with Q9-OME (A/G) and L24-OME with Q9-OME. Results of this experiment are shown in FIG. 12.

As expected, at 58° C., only the fluorescent signal from the G0 TaqMan® probe could be detected. At 75° C., fluorescent signals were detected from G0 and from L24/Q9-OME (A/G) but not from the two other tag-quenching oligonucleotide combinations. At 88° C., fluorescent signals could also be detected from L24-OME/Q9-OME (A/G) and at 97° C., signals were detected from all the probes, including the L24-OME/Q9-OME combination. These results show not only that fluorescent readings from three separate temperatures can be achieved using tagged probes and quenching molecules but that nucleotide modifications such as 2'-OMe can be selectively introduced to the nucleotide sequence of the tag portion or to the quenching oligonucleotide or to both in order to alter the melting temperature of the tag-quenching oligonucleotide duplex without having to change either their sequences or their lengths.

While the foregoing invention has been described in some detail for purposes of clarity and understanding, it will be clear to one skilled in the art from a reading of this disclosure that various changes in form and detail can be made without departing from the true scope of the invention. For example, the methods described above can be used in various combinations. All publications, patents, patent applications, and/or other documents cited in this application are incorporated by reference in their entirety for all purposes to the same extent as if each individual publication, patent, patent application, and/or other document were individually indicated to be incorporated by reference for all purposes.

```
INFORMAL SEQUENCE LISTING
SEQ ID NO 1: 9FAM9TAG oligonucleotide sequence
CGTCGCCAGTCAGCTCCGGT SEQ ID NO 2: Q0 quenching oligonucleotide
sequence (no quencher)
CCGGAGCTGACTGGCGACG SEQ ID NO 3: Q1 quenching oligonucleotide
sequence (BHQ-1 quencher on 5' terminus)
CCGGAGCTGACTGGCGACG SEQ ID NO 4: G0 TaqMan probe oligonucleotide
sequence (FAM/BHQ/phosphate)
TGCGCGTCCCGTTTTGATACTTCGTAACGGTGC SEQ ID NO 5: L24 Tagged probe oligonucleotide
sequence (BHQ/FAM/phosphate)
TCTCTAGCAGTGGCGCCCGAACAGGGACCACACATTGGCACCGCCGTCT SEQ ID NO 6: Q9 quenching oligonucleotide
sequence (quencher on 3' terminus)
AGACGGCGGTGCCAATGTGTG
```

The invention claimed is:

1. A kit for detecting two or more target nucleic acid sequences in a sample by a real-time polymerase chain reaction (PCR) assay comprising:
   (a) two or more pairs of oligonucleotide primers with sequences that are complementary to each strand of the two or more target nucleic acid sequences;
   (b) at least one oligonucleotide probe comprising two distinct portions: (i) an annealing portion comprising a sequence at least partially complementary to one of the two or more target nucleic acid sequences and anneals within said one of the two or more target nucleic acid sequences, wherein the annealing portion comprises a first quencher moiety; and (ii) a tag portion attached to the 5' terminus or to the 3' terminus of the annealing portion or attached via a linker between the 5' terminus and the 3' terminus of the annealing portion, and comprising a nucleotide sequence that is non-complementary to said one of the two or more target nucleic acid sequences, wherein the tag portion comprises a fluorescent moiety whose detectable signal is capable of being quenched by the first quencher moiety on the annealing portion, wherein said fluorescent moiety is separated from the first quenching moiety by a nuclease susceptible cleavage site;

(c) at least one quenching oligonucleotide comprising a nucleotide sequence at least partially complementary to the tag portion of the oligonucleotide probe and hybridizes to the tag portion to form a duplex, wherein said quenching oligonucleotide comprises a second quencher moiety which quenches the detectable signal generated by the fluorescent moiety on the tag portion when the quenching oligonucleotide is hybridized to the tag portion; and (d) a nucleic acid polymerase having 5' to 3' nuclease activity.

2. The kit of claim 1 wherein the tag portion is attached to the 5' terminus of the annealing portion.

3. The kit of claim 1 wherein the tag portion is attached via a linker between the 5' terminus and the 3' terminus of the annealing portion.

4. The kit of claim 1 wherein the tag portion of the oligonucleotide probe or the quenching oligonucleotide or both the tag portion of the oligonucleotide probe and the quenching oligonucleotide contains one or more nucleotide modifications.

5. The kit of claim 4 wherein the one or more nucleotide modifications comprises a nucleotide modification selected from Locked Nucleic Acid (LNA), Peptide Nucleic Acid (PNA), Bridged Nucleic Acid (BNA), 2'-O alkyl substitution, L-enantiomeric nucleotide, or combinations thoreof.

6. The kit of claim 5 wherein the nucleotide modification comprises LNA.

7. The kit of claim 5 wherein the nucleotide modification comprises PNA.

8. The kit of claim 5 wherein the nucleotide modification comprises BNA.

9. The kit of claim 5 wherein the nucleotide modification comprises L-enantiomeric nucleotide.

10. The kit of claim 9 wherein the nucleotide modification comprises L-enantiomeric LNA (L-LNA).

11. The kit of claim 5 wherein the nucleotide modification comprises 2'-O alkyl substitution.

12. The kit of claim 11 wherein the nucleotide modification comprises 2'-O methyl substitution (2'-OMe).

\* \* \* \* \*

SEQUENCE LISTING

```
<160> NUMBER OF SEQ ID NOS: 6

<210> SEQ ID NO 1
<211> LENGTH: 20
<212> TYPE: DNA
<213> ORGANISM: Artificial Sequence
<220> FEATURE:
```

```
<223> OTHER INFORMATION: 9FAM9TAG oligonucleotide sequence

<400> SEQUENCE: 1
cgtcgccagt cagctccggt                                              20

<210> SEQ ID NO 2
<211> LENGTH: 19
<212> TYPE: DNA
<213> ORGANISM: Artificial Sequence
<220> FEATURE:
<223> OTHER INFORMATION: Q0 quenching oligonucleotide

<400> SEQUENCE: 2
ccggagctga ctggcgacg                                               19

<210> SEQ ID NO 3
<211> LENGTH: 19
<212> TYPE: DNA
<213> ORGANISM: Artificial Sequence
<220> FEATURE:
<223> OTHER INFORMATION: Q1 quenching oligonucleotide (BHQ-1 on 5'
      terminus)

<400> SEQUENCE: 3
ccggagctga ctggcgacg                                               19

<210> SEQ ID NO 4
<211> LENGTH: 33
<212> TYPE: DNA
<213> ORGANISM: Artificial Sequence
<220> FEATURE:
<223> OTHER INFORMATION: G0 TaqMan probe oligonucleotide

<400> SEQUENCE: 4
tgcgcgtccc gttttgatac ttcgtaacgg tgc                               33

<210> SEQ ID NO 5
<211> LENGTH: 49
<212> TYPE: DNA
<213> ORGANISM: Artificial Sequence
<220> FEATURE:
<223> OTHER INFORMATION: L24 Tagged probe oligonucleotide

<400> SEQUENCE: 5
tctctagcag tggcgcccga acagggacca cacattggca ccgccgtct              49

<210> SEQ ID NO 6
<211> LENGTH: 21
<212> TYPE: DNA
<213> ORGANISM: Artificial Sequence
<220> FEATURE:
<223> OTHER INFORMATION: Q9 quenching oligonucleotide

<400> SEQUENCE: 6
agacggcggt gccaatgtgt g                                            21
```